United States Patent [19]

Fortin et al.

[11] Patent Number: 5,470,867

[45] Date of Patent: Nov. 28, 1995

[54] IMIDAZOLES AND THEIR SALTS HAVING ANTHGONISTIC ACTIVITY TO ANGIOTESIN II RECETORS

[75] Inventors: Michel Fortin; Daniel Frechet, both of Paris; Gilles Hamon, Le Raincy; Simone Jouquey, Paris; Jean-Paul Vevert, Pantin, all of France

[73] Assignee: Roussel-Uclaf, France

[21] Appl. No.: 324,772

[22] Filed: Oct. 17, 1994

Related U.S. Application Data

[62] Division of Ser. No. 74,106, Jun. 9, 1993, Pat. No. 5,389,634, which is a division of Ser. No. 712,247, Jun. 7, 1991, Pat. No. 5,338,756.

[30] Foreign Application Priority Data

Jun. 8, 1990 [FR] France .................................. 90 67136
Mar. 13, 1991 [FR] France .................................. 91 03032

[51] Int. Cl.$^6$ ...................... A61K 31/435; A61K 31/505; A61K 31/41; C07D 471/04; C07D 495/04; C07D 487/04
[52] U.S. Cl. ........................ 514/393; 514/397; 514/402; 548/303.7; 548/304.1
[58] Field of Search ............................. 548/303.7, 304.1; 514/397, 402, 393

[56] References Cited

U.S. PATENT DOCUMENTS

| 5,338,756 | 8/1994 | Fortin et al. | 54/394 |
| 5,389,634 | 2/1995 | Fortin et al. | 514/248 |

FOREIGN PATENT DOCUMENTS

| 0483683 | 5/1992 | European Pat. Off. | 548/303.7 |
| 0518033 | 12/1992 | European Pat. Off. | 548/303.7 |

Primary Examiner—Floyd D. Higel
Attorney, Agent, or Firm—Bierman and Muserlian

[57] ABSTRACT

Imidazoles of the formula

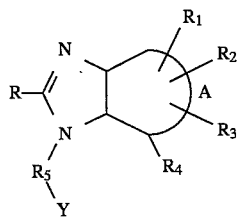

and their non-toxic, pharmaceutically acceptable salts with acids and bases having an antagonistic activity against angiotensin II receptors.

8 Claims, No Drawings

IMIDAZOLES AND THEIR SALTS HAVING ANTHGONISTIC ACTIVITY TO ANGIOTESIN II RECETORS

PRIOR APPLICATION

This application is a division of U.S. patent application Ser. No. 074,106, filed Jun. 9, 1993, now U.S. Pat. No. 5,389,634, which is a division of U.S. patent application Ser. No. 712,247, filed Jun. 7, 1991, now U.S. Pat. No. 5,338, 756.

OBJECTS OF THE INVENTION

It is an object of the invention to provide the novel compounds of formula I and their non-toxic, pharmaceuticlly acceptable salts with acids and bases and novel processes and intermediates for the preparation thereof.

It is a further object of the invention to provide compositions and method for inducing antagonistic activity to angiotensin II receptors.

These and other objects and advantages will become obvious from the following detailed description.

THE INVENTION

The novel compounds of the invention are selected from the group consisting of all possible racemic, enantiomeric and diasterisomeric forms of a compound of the formula

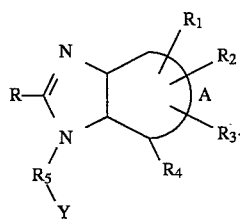

I wherein A is the remainder of a monocyclic group of 3, 4 or 5 links or a condensed ring of 6 to 12 links optionally unsaturated and optionally containing at least one heteroatom selected from the group consisting of —O—, optionally oxidized nitrogen and optionally oxidized sulfur, R is selected from the group consisting of alkyl of 1 to 6 carbon atoms and alkenyl and alkynyl of 2 to 6 carbon atoms, all optionally substituted, $R_1$, $R_2$, $R_3$ and $R_4$ are individually selected from the group consisting of a) hydrogen, halogen, hydroxy, cyano, nitro, sulfo, formyl, benzoyl, acyl and acyloxy of up to 12 carbon atoms, free, salified or esterified carboxy and —SH, b) alkyl, alkoxy and alkylthio of 1 to 6 carbon atoms and alkenyl and alkynyl of 1 to 6 carbon atoms, all optionally substituted, c) aryl, aralkyl of 1 to 6 alkyl carbon atoms and aralkenyl of 2 to 6 alkenyl carbon atoms, the aryl being monocyclic of 5 to 6 links or condensed cyclic of 8 to 14 links optionally containing at least one heteroatom of the group consisting of oxygen, nitrogen or sulfur atom, all optionally substituted,

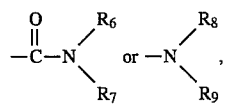 d)

$R_6$ and $R_7$ or $R_8$ and $R_9$ are individually selected from the group consisting of a) hydrogen, b) alkyl and alkenyl of up to 6 carbon atoms and optionally substituted with a halogen, —OH or alkoxy of 1 to 6 carbon atoms, c) aryl and aralkyl of 1 to 6 alkyl carbon atoms and the aryl is monocyclic of 5 to 6 links or condensed ring of 8 to 14 links, both optionally containing at least one heteroatom of nitrogen, oxygen or sulfur and optionally substituted with at least one member of the group consisting of halogen, —OH, —NO$_2$, alkyl and alkoxy of 1 to 6 carbon atoms, alkenyl of 2 to 6 carbon atoms, acyl of 1 to 6 carbon atoms and free, salified or esterified carboxy and d) —(CH$_2$)$_m$—SO$_2$—X—R$_{14}$, m is 0 to 4, X—R$_{14}$ is —NH$_2$ or X is selected from the group consisting of F

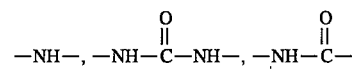

and a single bond and $R_{14}$ is selected from the group consisting of optionally substituted alkyl, alkenyl and aryl or $R_6$ and $R_7$ or $R_8$ and $R_9$ taken together with the nitrogen to which they are attached form a monocyclic of 5 to 6 links or a condensed ring of 8 to 14 links, both optionally containing at least one heterotom of nitrogen or oxygen or sulfur and optionally substituted with at least one member of the group consisting of halogen, —OH, —NO$_2$, alkyl and alkoxy of 1 to 6 carbon atoms, alkenyl of 2 to 6 carbon atoms, acyl of 1 to 6 carbon atoms and free, salified or esterified carboxy or $R_8$ and $R_9$ are individually selected from the group consisting of acyl of a carboxylic acid of 1 to 6 carbon atoms, alkylsulfonyl of 1 to 6 alkyl carbon atoms and arylsulfonyl of 6 to 8 carbon atoms, all optionally substituted with at least one member of the group consisting of halogen and alkyl of 1 to 6 carbon atoms and e) —(CH$_2$)$_m$—SO$_2$—X—R$_{14}$ wherein m, X and R$_{14}$ have the above definitions, $R_5$ is an alkylene of 1 to 4 carbon atoms, Y is —Y$_1$B—Y$_2$, Y$_1$ is a monocyclic aryl of 5 to 6 links or a condensed ring of 8 to 10 links, both optionally containing at least one nitrogen or oxygen or sulfur heteroatom and optionally substituted by at least one of the groups of $R_1$, $R_2$, $R_3$ and $R_4$ definition, B is a member of the group consisting of a single bond,

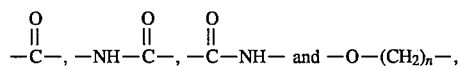

n is 0 to 3 and when B is other than a single bond, Y$_2$ has a definition of Y$_1$ and when B is a single bond, Y$_2$ is selected from the group consisting of hydrogen, —CN and free, salified or esterified carboxy with the proviso that when A is phenyl optionally substituted with 1 to 2 members of the group consisting of halogen, penta-fluorophenyl, free carboxy, optionally substituted alkenyl, alkoxy and acyl and R$_5$ is —CH$_2$— and Y is —Y$_1$—B—Y$_2$, Y$_1$ is phenyl and Y$_2$ is phenyl ortho substituted with optionally salified carboxy or tetrazolyl or trifluoromethylsulfonamido and optionally containing a second substituent selected from the group consisting of halogen, alkyl of 1 to 4 carbon atoms, —NO$_2$ and —OCH$_3$, B is

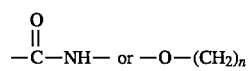

and n is 2 or 3 and non-toxic, pharmaceutically acceptable salts with acids or bases.

In the compounds of formula I, the monocyclic ring and condensed rings include saturated and unsaturated carbocyclic and heterocyclic groups with the latter containing at least one nitrogen, oxygen or sulfur heteroatom. The monocyclic ring preferably has 5 to 6 links or ring members and when A is the remainder of a monocyclic ring, the remainder has 3 to 4 links. Examples of saturated monocyclic carbocyclic rings are cyclohexyl and cyclopentyl and cycloheptyl and examples of unsaturated monocyclic carbocyclic rings are cyclopentenyl, cyclohexenyl, cycloheptenyl, cyclopentadienyl, cyclohexadienyl and carbocyclic aryl such as phenyl.

Examples of saturated monocylic heterocyclics are pyrrolidinyl, imidazolidinyl, pyrazolidinyl, piperidyl, piperazinyl or morpholinyl and examples of unsaturated monocyclic heterocyclics are aryl such as thienyl, furyl, pyranyl, pyrrolyl, imidazolyl, pyrazolyl, pyridyl, pyrazinyl, pyrimidinyl, pyridazinyl, thiazolyl, azepine, oxazolyl, furazanyl, pyrrolinyl such as delta 2-pyrrolinyl, imidazolinyl such as delta 2-imidazolinyl, pyrazolinyl such as delta 3-pyrazolinyl, as well as the position isomers of the hetero-atom or heteroatoms that these radicals can contain such as iso-thiazolyl, isoxazolyl, tetrazolyl, thiadiazolyl, triazolyl (1,2,3-or 1,3,4- triazolyl), cyanotriazolyl, carboxy triazolyl, methoxycarbonyltriazolyl and trifluoromethyltriazolyl.

The condensed rings preferably contain 8 to 14 links and the remainder of a condensed ring thus preferably designating remainders containing 6 to 12 links. Examples of saturated carbocyclic condensed rings is bicyclo-(4,4,0)-decyl, bicyclo-(4,4,1)-undecyl. Examples of unsaturated carbocyclic condensed rings are aryl radicals such as naphthyl and phenanthryl.

Examples of saturated heterocyclic condensed rings are oxa-1-spiro(4,5)decane, tetrahydropyran-2-spirocyclohexane, spiro-2'-(tetrahydrofuran) and 1,10-diaza-4-anthryl. Examples of unsaturated heterocyclic condensed rings are benzothienyl, naphtho (2,3-b)thienyl, indane, indenyl, thianthrenyl, isobenzofuranyl, chromenyl, xanthenyl, phenoxathiinyl, indolizinyl, iso-indolyl, 3H-indolyl, indolyl, indazolyl, purinyl, quinolizinyl, isoquinolyl; quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl and also condensed polycyclic systems composed of monocyclic heterocyclics as defined above for example, furo(2,3-b)pyrrole or thieno(2,3-b)furan.

When A is the remainder of a monocyclic of 3 to 4 links or of a condensed ring of 6 to 12 links, A may be a remainder of 5 to 6 links or 8 to 14 links respectively and can be saturated or unsaturated, carbocyclic or heterocyclic having at least one oxygen, nitrogen or sulfur heteroatom and when these heterocyclics contain more than one heteroatom, the heteroatoms of these heterocyclic radicals can be identical or different.

In the compounds of formula I, the sulfur atom can be an oxide in the form of sulfoxide or sulfone and examples of linear or branched alkyl are methyl, ethyl, n-propyl, isopropyl, n-butyl, isobutyl, sec-butyl and tert-butyl as well as pentyl or hexyl and particularly isopentyl or isohexyl. Examples of linear or branched alkenyl are vinyl, allyl, 1-propenyl, butenyl and especially buten-1-yl or pentenyl. Examples of linear or branched alkynyl are ethynyl, propargyl, butynyl and pentynyl.

The halogen is preferably chlorine but can also be fluorine, bromine or iodine. Examples of acyl of 2 to 6 carbon atoms are acetyl, propionyl, butyryl and benzoyl, as well as valeryl, hexanoyl, acryloyl, crotonoyl and carbamoyl. Examples of acyloxy are one of the acyls as defined above and linked to an oxygen atom, such as acetoxy or benzoyloxy.

Esterified carboxy preferably is a lower alkoxycarbonyl such as methoxycarbonyl, ethoxycarbonyl, tert-butoxycarbonyl or benzyloxycarbonyl. Examples of alkoxy are methoxy and ethoxy as well as propoxy, isopropoxy, linear, secondary or tertiary butoxy. Examples of linear or branched alkylthio are the alkyls indicated above for the alkyl and alkylthio. Preferred is methylthio or ethylthio, but can also be propylthio, isopropylthio, n-butylthio, sec-butylthio, tert-butylthio, isopentylthio and isohexylthio.

Examples of aryls are unsaturated monocyclic or condensed rings, carbocyclic or heterocyclic which can contain one or more heteroatoms of oxygen, nitrogen or sulfur and when these heterocyclics contain more than one heteroatom, the heteroatoms of these heterocyclic can be identical or different such as aryl are phenyl, naphthyl, thienyl such as thien-2-yl and thien-3-yl, furyl such as fur-2-yl, pyridyl such as pyrid-3-yl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; condensed heterocyclic groups containing at least one heteroatom chosen from sulfur, nitrogen and oxygen are benzothienyl such as benzothien-3-yl, benzofuryl, benzopyrrolyl, benzimidazolyl, benzoxazolyl, thionaphthyl, indolyl or purinyl. Preferred are phenyl and tetrazolyl.

The aryls can be optionally substituted such as N-substituted pyrrolyl like N-methylpyrrolyl, substituted 3- or 4-isoxazolyl like 3-aryl-5-methylisoxazol-4-yl, the aryl group being phenyl or halophenyl. Among the substituents of the aryl radicals and tetrazolyl are alkyl, alkenyl and alkoxy of at most 4 carbon atoms and alkoxyalkyl or arylalkyl such as benzyl optionally substituted by nitro, methoxy, hydroxyl, amino or halogen.

The arylalkyl and arylalkenyl have alkyl, alkenyl and aryl respectively as defined above. Examples of such arylalkyl are benzyl, diphenylmethyl, triphenylmethyl, naphthylmethyl, indenylmethyl, thienylmethyl such as thien-2-ylmethyl, furylmethyl such as furfuryl, pyridylmethyl, pyrimidylmethyl or pyrrolylmethyl. It is to be understood that in the non-exhaustive list of examples as cited above, the alkyl can be represented quite as well by ethyl, propyl or butyl such as in phenethyl.

Examples of arylalkenyl are those of arylalkyl given above in which the alkyl is replaced by alkenyl such as phenylvinyl or phenylallyl. It is understood that in these, the phenyl can be replaced by naphthyl or pyridyl or also one of the aryl as defined above in the non-exhaustive list of aralkyls.

The alkyl, alkenyl and alkynyl as defined above as well as the alkyl or alkenyl of the alkylthio, arylalkyl and arylalkenyl as defined above can be non-substituted or carry at least one substituent selected from the group consisting of halogen such as chloro or bromo, as in 2-bromoethyl; hydroxyl; aryl as defined above such as monocyclic or carbocyclic or heterocyclic condensed rings, it being understood that the heterocyclic as defined above can contain one or more heteroatoms chosen from oxygen, nitrogen or sulfur atoms and that when these heterocyclic radicals contain more than one heteroatom, the heteroatoms of these heterocyclics can be identical or different, the heterocyclic being able to be linked by a carbon or, if appropriate, by a nitrogen. Examples of arylalkyl in which the aryl is as defined above are cycloalkyl such as cyclopropyl, cyclopentyl or cyclohexyl; cycloalkenyl such as cyclohexenyl optionally substituted, among which is 1,3-dimethyl cyclohexene; alkoxy as defined above, for example methoxy, ethoxy, n-propoxy or iso-propoxy; alkoxyalkyl such as methoxymethyl or 1-ethoxyethyl; substituted alkoxy such as trihaloalkoxy like trifluoromethoxy; aryloxy such as phenoxy; aralkoxy such as benzyloxy; mercapto; alkylthio like methylthio or ethylthio; substituted alkylthio such as trihloalkylthio like trifluoromethyltio; arylthio; aralkylthio; amino as in 2-aminoethyl; amino substituted by one or two members chosen for example from alkyl, alkenyl, aryl and arylalkyl as defined above such as monoalkylamino like methylamino or ethylamino, dialkylamino or ethylamino, dialkylamino such as dimethylamino; nitro; cyano; azido; carboxy; esterified carboxy such as methoxy-carbonyl or ethoxy-carbonyl; formyl; acyl such as acetyl, propionyl or benzoyl; acyl substituted for example by an amino as defined above or by a cyclic linked to the acyl by a nitrogen atom, the cyclic being able to contain optionally one or more heteroatoms chosen from nitrogen, oxygen or sulfur and as defined above; acyloxy such as acetoxy or propionyloxy; carbamoyl; substituted carbamoyl such as lower N-monoalkyl carbamoyl such as N-methylcarbamoyl, N-ethylcarbamoyl, a lower N,N-dialkylcarbamoyl such as N,N-dimethylcarbamoyl, N,N-diethylcarbamoyl; an N-(lower hydroxyalkyl)carbamyl such as N-(hydroxymethyl)carbamoyl, N-(hydroxyethyl)carbamoyl, lower carbamoylalkyl group such as carbamoylmethyl, carbamoylethyl; phthalimido; acylamido such as acetamido or benzamido; alkoxycarbonylamino like methoxycarbonylamino or ethoxycarbonylamino; or aralkoxycarbonylamino like benzyloxycarbonylamino.

The aryl and alkoxy as defined above and the aryl of the arylalkyl and arylalkenyl as defined above can be non-substituted or carry one or more substituents chosen from the list indicated above for the possible substituents of the alkyl, alkenyl and alkynyl as defined above, for example o-chlorophenyl, but can also be substituted by one or more members chosen from the group formed by alkyl such as lower alkyl, methyl, ethyl or isopropyl or tert-butyl; alkenyl; substituted alkyl such as trihaloalkyl as in trifluoromethyl; alkenyl such as vinyl or allyl; alkynyl such as propargyl.

The amino that can be represented by one or more of the possible substituents as defined in the products of formula I and in what follows and that can be represented in particular by

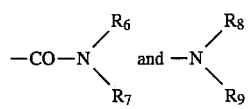

wherein $R_6$ and $R_7$ or $R_8$ and $R_9$ are two individual groups linked to the nitrogen atom selected from the group consisting of hydrogen, alkyl as defined above, preferably monolkyl- or dialkylamino in which the alkyls contain 1 to 6 carbon atoms and particularly methyl, ethyl, isopropyl, trifluoromethyl, pentafluoroethyl, hydroxymethyl, hydroxyethyl, methoxymethyl, methoxyethyl, ethoxyethyl; alkenyl as defined above and preferably vinyl and allyl; aryl or arylalkyl as defined above, carbocyclic or heterocyclic and particularly phenyl, benzyl, phenethyl, naphthyl, indolyl, indolinyl, thienyl, furyl, pyrrolyl, pyridyl, pyrrolidinyl, piperidino, morpholino, piperazinyl, optionally substituted by one or more radicals as defined above such as methylpiperazinyl, fluoromethylpiperazinyl, ethylpiperazinyl, propylpiperazinyl, phenylpiperazinyl or benzylpiperazinyl.

When $R_6$ and $R_7$ on the one hand and $R_8$ and $R_9$ on the other hand form together with the nitrogen atom to which they are linked a heterocycle, examples are pyrrolyl, imidazolyl, pyridyl, pyrazinyl, pyrimidyl, indolyl, indolinyl, purinyl, quinolyl, pyrrolidinyl, piperidyl, piperidino, morpholino, piperazinyl; optionally substituted by the substituents already mentioned previously and particularly by one or more of chlorine and fluorine, methyl, ethyl, isopropyl, tert-butyl, methoxy, ethoxy, propoxy, benzoyl, methoxycarbonyl, ethoxycarbonyl, such as methylpiperazinyl, ethylpiperazinyl, propylpiperazinyl, phenylpiperazinyl or benzylpiperazinyl. In these last two, phenyl and benzyl can be substituted as indicated previously for aryl, arylalkyl and arylalkenyl.

The acyls that can be $R_8$ and $R_9$ are as defined previously and can be chosen from acetyl, propionyl, butyryl, valeryl or carbamoyl. The alkyl or arylsulfonyl that can be represented by $R_8$ or $R_9$ are preferably methylsulfonyl, trifluoromethylsulfonyl or p-tolylsulfonyl.

$Y_1$ and $Y_2$ can have the values defined above for the monocyclic aryl or condensed rings, it being understood that in the case where B is a single bond, $Y_2$ can also be hydrogen, cyano or free, salified or esterified carboxy, being preferably lower alkoxycarbonyl such as methoxycarbonyl, ethoxycarbonyl or benzyloxycarbonyl.

$Y_1$ and $Y_2$ individually may be aryl optionally substituted by at least one member of the group of halogen, hydroxyl or nitro, alkyl, alkenyl, alkoxy, acyl and free, salified or esterified carboxy containing at most 6 carbon atoms and being as defined above.

The addition salts with mineral or organic acids of the products of formula I can be salts formed with hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids such as methanesulfonic acid, ethanesulfonic acid, propanesulfonic acid, alkyldisulfonic acids such as methanedisulfonic acid, ethanedisulfonic acid, arylmonosulfonic acids such as benzenesulfonic acid and aryldisulfonic acids.

The carboxys of the products of formula I can be salified by mineral bases such as an equivalent of sodium, potassium, lithium, calcium, magnesium or ammonium or organic bases such as methylamine, propylamine, trimethylamine, diethylamine, triethylamine, N,N-dimethylethanolamine, tris(hydroxymethyl)amino methane, ethanolamine, pyridine, picoline, dicyclohexylamine, morpholine, benzylamine, procaine, lysine, arginine, histidine, N-methylglucamine.

The $-(CH_2)_m-SO_2-X-R_{14}$ can be groups in which $(CH_2)_m$ is alkylene derived from the linear alkyl indicated above such as methylene, ethylene, n-propylene or butylene and $R_{14}$ may be alkyl or alkenyl chosen from the values defined above or an aryl chosen from the values indicated above such as phenyl, biphenyl, naphthyl, tetrazolyl. The alkyl which can be $R_{14}$ can optionally be substituted by aryl chosen from the values define above to form an aralkyl.

These alkyl, alkenyl, aryl and aralkyl can be substituted as is indicated above. Among the substituents which can be carried by $R_{14}$ when it is alkyl, alkenyl, aryl or aralkyl are:
—$PO_3H$, —PO(OH)alkyl, PO(OH)aryl, —PO(OH)alkoxy, amino, mono- or dialkylamino, free, esterified or salified carboxy, nitro, halogen, alkylthio, alkoxy, hydroxy, mercapto.

Examples in a non-exhaustive manner are:
—$SO_2$—$NH_2$, —$SO_2$—NH—$CH_3$, —$SO_2$—NH—$CF_3$,
—$SO_2$—NH—$C_6H_5$,
—$SO_2$—NH—$CH_2$—$C_6H_5$,
—$CH_2$—$SO_2$—$NH_2$, —$CH_2$—$SO_2$—NH—$C_6H_5$,
—$SO_2$—NH—CO—NH—$CH_3$,    —$SO_2$—NH—CO—NH—$C_6H_5$,
—$SO_2$—NH—CO—NH—$CF_3$, —$SO_2$—NH—CO—NH—$CH_2$—$C_6H_5$, —SO$_2$—NH—CO—NH—C$_6$H$_4$Cl,

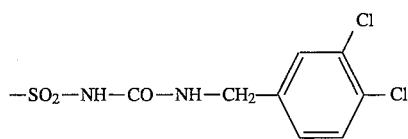

—SO$_2$—NH—CO—NH—CH=CH—CH$_3$,

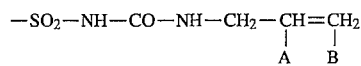

—SO$_2$—NH—CO—NH—CH=CH—CH$_3$,
in which A and B are individually chosen among hydrogen, phenyl, pyridyl and pyridinyl,

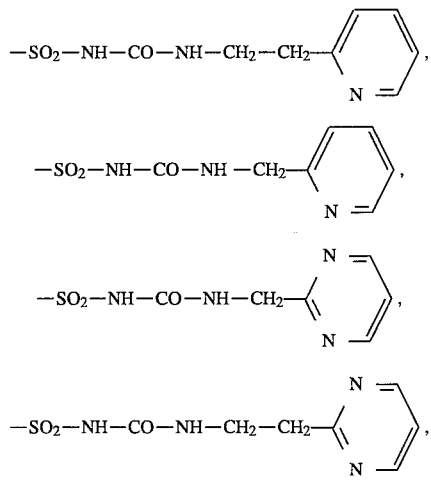

The aryl of Y$_1$ or Y$_2$ can be substituted by one or more of R$_1$, R$_2$, R$_3$ and R$_4$ and particularly by
—NH—(CH$_2$)$_m$—SO$_2$—X—R$_{14}$ and
—CO—NH—(CH$_2$)$_m$—SO$_2$—X—R$_{14}$ in which (CH$_2$)$_m$—SO$_2$—X—R$_{14}$ can take the values indicated above.

Y$_1$ or Y$_2$ can also be substituted by a free, esterified or salified carboxy, cyano, formyl or tetrazolyl, tetrazolylalkyl, preferably tetrazolylethyl or tetrazolylcarbamoyl.

All the groups indicated above are preferably situated in the ortho position and on only Y$_2$. Non-exhaustive examples are:
—NH—SO$_2$—CH$_3$, —NH—SO$_2$C$_6$H$_5$, —NH—SO$_2$—CF$_3$,
—NH—CH$_2$—SO$_2$—NH—C$_6$H$_5$,
—CO—NH—SO$_2$—C$_2$H$_5$, —CO—NH—SO$_2$—CH$_3$,
—CO—NH—SO$_2$—CH—C$_6$H$_5$.

Among the preferred products of formula I as defined above are those in which the individual substituent or substituents which can be carried by:

a) the alkyl, alkenyl and alkynyl of R, b) the alkyl, alkenyl, alkynyl, alkoxy and alkylthio of R$_1$, R$_2$, R$_3$ and R$_4$, c) the aryl, arylalkyl and arylalkenyl of R$_1$, R$_2$, R$_3$ and R$_4$ d) the alkyl, alkenyl and aryl of R$_{14}$ are chosen from the group formed by halogen, hydroxyl, cyano, nitro, formyl, acyl or acyloxy of at most 6 carbon atoms, benzoyl, carboxy free, salified or esterified by an alkyl of 1 to 6 carbon atoms, alkyl and alkenyl of at most 6 carbon atoms and optionally substituted by at least one substituent chosen from halogen, hydroxyl and alkoxy of 1 to 6 carbon atoms, linear and branched alkoxy of 1 to 6 carbon atoms, aryl and arylalkyl in which the alkyl contains 1 to 6 carbon atoms, these aryl and arylalkyl being such that the aryl is a monocyclic of 5 to 6 links or condensed ring containing 8 to 14 links both optionally containing one or more heteroatoms chosen from oxygen, nitrogen and sulfur and optionally substituted by one or more members chosen from halogen, hydroxyl, nitro, alkyl, alkenyl, alkoxy and acyl of at most 6 carbon atoms, free, salified or esterified carboxy,

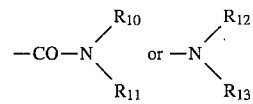

wherein either R$_{10}$ and R$_{11}$ or R$_{12}$ and R$_{13}$ individually are hydrogen, alkyl or alkenyl of at most 6 carbon atoms and optionally substituted by one or more substituents chosen from halogen, hydroxyl and alkoxy of 1 to 6 carbon atoms, aryl or arylalkyl in which the linear or branched alkyl contains 1 to 6 carbon atoms, the aryl and arylalkyl being such that the aryl is a monocyclic containing 5 to 6 links or condensed ring containing 8 to 14 links optionally containing one or more heteroatoms chosen from oxygen, nitrogen and sulfur and optionally substituted by one or more members chosen from halogen, hydroxyl, nitro, alkyl, alkenyl, alkoxy and acyl containing at most 6 carbon atoms, free, salified or esterified carboxy, tetrazolyl, tetrazolylmethyl and tetrazolylcarbamoyl, or R$_{10}$ and R$_{11}$ or R$_{12}$ and R$_{13}$ form respectively with the nitrogen atom to which they are linked a monocyclic containing 5 to 6 links or a condensed ring containing 8 to 14 links, both optionally containing one or more heteroatoms chosen from oxygen, nitrogen and sulfur and optionally substituted by one or more members chosen from halogen, hydroxyl, nitro, alkyl, alkenyl, alkoxy and acyl containing at most 6 carbon atoms, free, salified or esterified carboxy, tetrazolyl, tetrazolylmethyl and tetrazolylcarbamoyl, or R$_{12}$ and R$_{13}$ individually are acyl of a carboxylic acid of 1 to 6 carbon atoms, said products of formula I being in all possible racemic, enantiomeric and diastereoisomeric isomer forms, as well as the addition salts with mineral and organic acids or with mineral and organic bases of said products of formula I.

Among the substituents on the alkyl, alkenyl, alkynyl, alkoxy, alkylthio, aryl, arylalkyl and arylalkenyl as defined above are preferably halogen such as chloro and bromo; hydroxyl; acyl such as acetyl, propionyl, butyryl, valeryl, hexanoyl, acryloyl, crotonoyl or carbamoyl; benzoyl; esterified carboxy preferably a lower alkoxy carbonyl such as methoxycarbonyl, ethoxycarbonyl or benzyloxycarbonyl; alkyl such as methyl or ethyl; amino; substituted amino such as monoalkylamino and dialkylamino like methylamino, ethylamino or dimethylamino; alkoxy such as methoxy, ethoxy or isopropoxy; aryl such as phenyl, biphenyl, naphthyl, indenyl, indolyl or indolinyl; aralkyl such as benzyl or phenethyl; alkyl, alkoxy and aryl as defined above optionally may be substituted by one or more individual members selected from the group consisting of hydroxy, linear or branched alkyl and alkoxy such as methyl, ethyl, tert-butyl, methoxy, ethoxy, isopropoxy; substituted amino such as monoalkyl- and dialkylamino like methylamino, ethylamino or dimethylamino.

Examples of groups in which A is a remainder as defined above, are the monocyclic carbocyclic or heterocyclic containing 6 links such as phenyl, pyrannyl, pyridyl, pyrimidinyl, pyridazinyl, pyrazinyl, piperidyl, piperazinyl, piperidino and morpholino; the monocyclic, carbocyclic or heterocyclic containing 5 links, such as furyl, pyrrolyl, pyrrolinyl, imidazolyl, pyrazolyl, isothiazolyl, isoxazolyl, pyrrolidinyl, imidazolidinyl or pyrazolidinyl; the carbocyclic or heterocyclic condensed rings such as naphthyl, indolyl, quinolyl or purinyl as well as their position isomers of the heteroatom or atoms, for example, nitrogen, such as imidazolyl or isoquinolyl.

When the heterocycle in which A contains one or more nitrogen atoms which can be non-substituted or substituted by a linear or branched alkyl or alkoxy of 1 to 5 carbon atoms, as defined above such as methyl, ethyl, isopropyl, tert-butyl, methoxy or ethoxy, phenyl or benzyl optionally substituted by the substituents mentioned above for the aryl and arylalkyl. Examples are methylpiperazinyl, ethylpiperazinyl, propylpiperazinyl, phenylpiperazinyl or benzylpiperazinyl. Among the preferred values of A are phenyl, naphthyl, pyridyl, piperazinyl, pyrimidinyl, pyridazinyl and pyrazinyl.

A preferred group of compounds of formula I are those of the formula

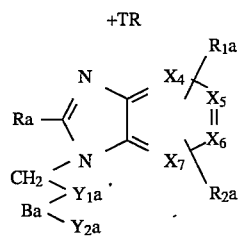

Ia wherein $X_4$, $X_5$, $X_6$ and $X_7$ are all methine =CH or any one or two of them is nitrogen atom and the others are methine, $R_a$ is n-butyl or butenyl, $R_{1a}$ and $R_{2a}$ are individually selected from the group of hydrogen, halogen, hydroxyl, mercapto, alkoxy of 1 to 6 carbon atoms, alkyl, alkenyl, alkynyl and alkylthio of at most 6 carbon atoms and aryl, arylalkyl or arylalkenyl in which the alkyl and alkenyl contain at most 6 carbon atoms, these aryl, arylalkyl and arylalkenyl being such that the aryl is a monocyclic of 5 to 6 links or a condensed ring of 8 to 14 links, optionally containing at least one heteroatom chosen from oxygen, nitrogen or sulfur and all alkoxy, alkyl, alkenyl, alkynyl, alkylthio, aryl, arylalkyl and arylalkenyl being optionally substituted by at least one member of the group consisting of halogen, hydroxyl, alkyl, alkoxy or alkylthio of 1 to 6 carbon atoms, mercapto, acyl, acyloxy, tetrazolyl, free carboxy, carboxy esterified by alkyl of 1 to 4 carbon atoms, $Y_{1a}$ is phenyl, $B_a$ is a single bond or a —CO—NH—, $Y_{2a}$ is such that:either, if $B_a$ is single bond or —CO—NH—, $Y_{2a}$ is phenyl optionally substituted by at least one member of the group of $R_{1a}$ and $R_{2a}$, or if $B_a$ is a single bond, $Y_{2a}$ is cyano or free, salified or esterified carboxy, or tetrazolyl, it being understood that if $B_a$ is single bond, then at least one of $X_4$, $X_5$, $X_6$ and $X_7$ is not methine, said products of formula I being in all possible racemic, enantiomeric and diastereoisomeric isomer forms, as well as the addition salts with mineral and organic acids or with mineral or organic bases of said products of formula I.

A more preferred group of compounds of formula I are those corresponding to formula $I_a$ in which $X_4$, $X_5$, $X_6$, $X_7$, $R_a$, $R_{1a}$ and $R_{2a}$ have the above meanings and $Y_{1a}$ is phenyl, $B_a$ is a single bond or —CO—NH— and $Y_{2a}$ is such that: if $B_a$ is a single bond or —CO—NH—, $Y_{2a}$ is phenyl optionally substituted by —$(CH_2)_p$—$SO_2$—$X_a$—$R_{14a}$ in which p is 0 or 1, $X_a$ is —NH—, —NH—CO—, —NH—CO—NH— or a single bond and $R_{14a}$ is methyl, ethyl, vinyl, allyl, pyridylmethyl, pyridylethyl, pyridyl, phenyl or benzyl, free, salified or esterified carboxy, tetrazolyl, tetrazolylalkyl or tetrazolylcarbamoyl in which the tetrazolyl is optionally substituted by an alkyl, alkenyl, arylalkyl or alkoxyalkyl and if $B_a$ is a single bond, $Y_{2a}$ is cyano or free, salified or esterified carboxy, or tetrazolyl, with the proviso that if $B_a$ is a single bond, then at least one of $X_4$, $X_5$, $X_6$ and $X_7$ is not methine said products of formula I being in all possible racemic, enantiomeric and diastereoisomeric isomer forms, as well as the addition salts with mineral and organic acids or with mineral and organic bases of said products of formula I.

When $R_{1a}$ or $R_{2a}$ is alkoxy, it may be methoxy, ethoxy or isopropoxy and; when $R_{1a}$ or $R_{2a}$ is substituted alkyl, it may be methyl, ethyl, isopropyl or tert-butyl optionally substituted by one or more members chosen preferably from the group of halogen such as bromine, chlorine or fluorine as for example trifluoromethyl and hydroxyl or alkoxy of 1 to 4 carbon atoms such as methoxy, ethoxy or isopropoxy. When $R_{1a}$ or $R_{2a}$ are esterified carboxy, it may be methoxycarbonyl or ethoxycarbonyl.

Examples of A are:

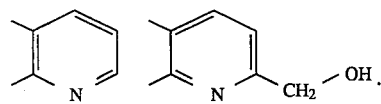

Among the preferred values of the ring

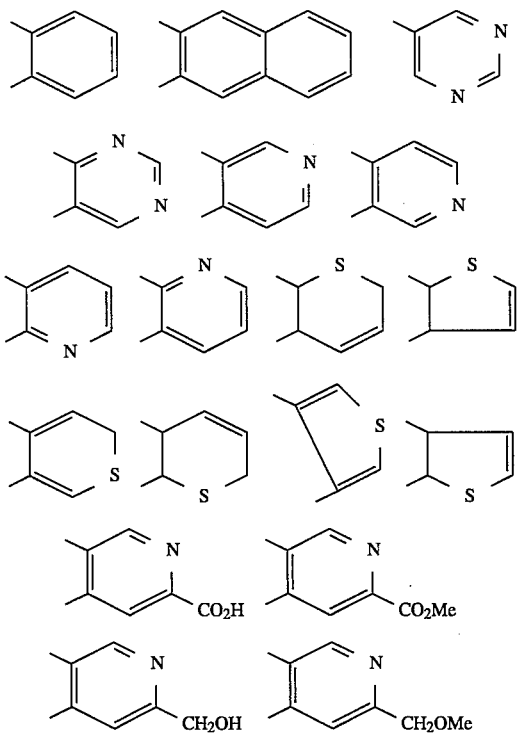

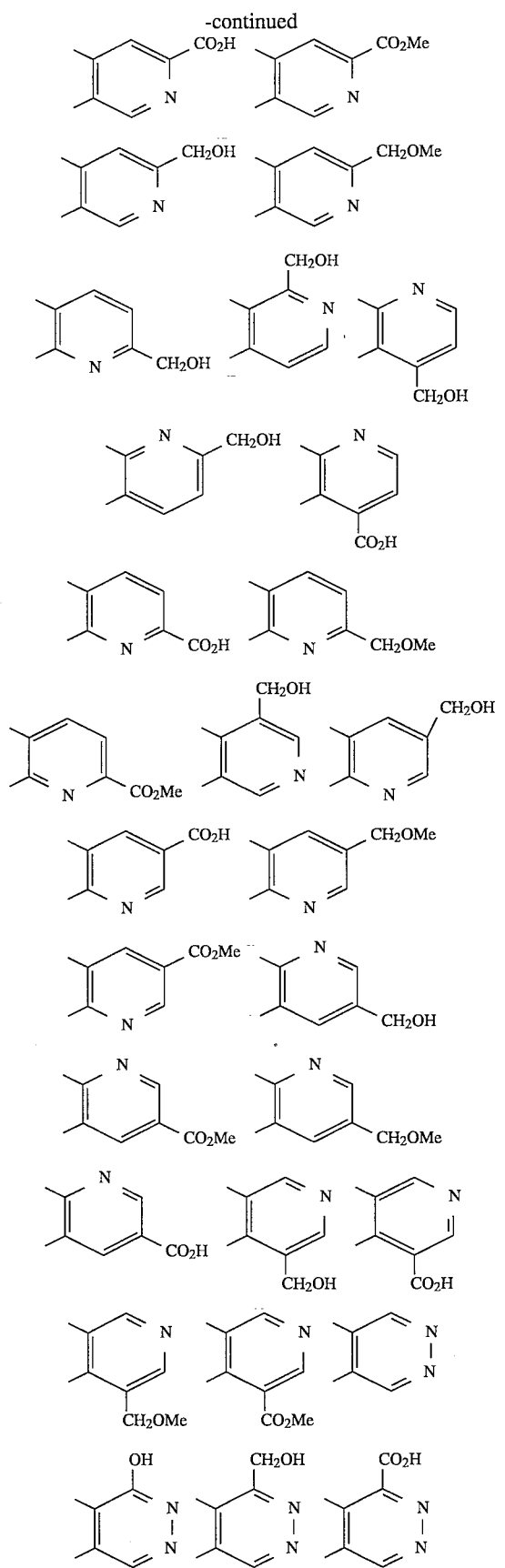
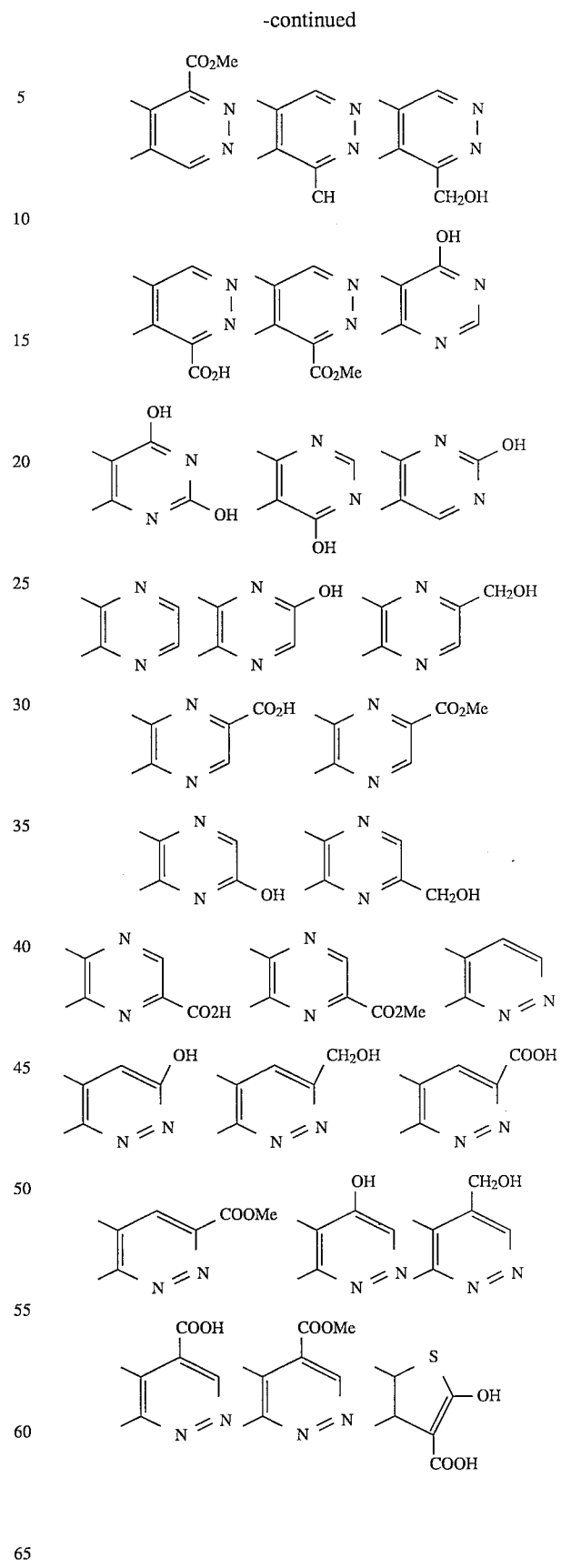

-continued

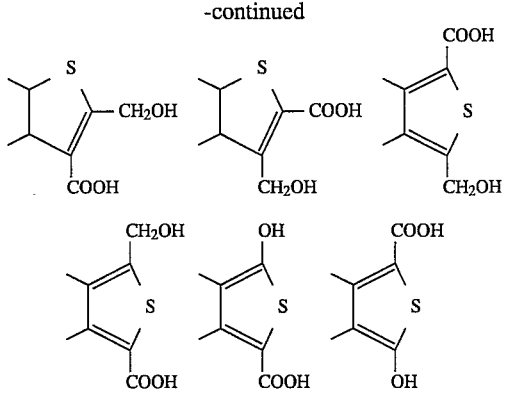

Most preferrably, A is phenyl, naphthyl, pyridyl, pyrimidinyl or thienyl, R is n-butyl or buten-1-yl, $R_1$, $R_2$, $R_3$ and $R_4$ are such that two of them are hydrogen and the other two are individually hydrogen, hydroxyl, alkyl of 1 to 4 carbon atoms, carboxy free or esterified by an alkyl of 1 to 4 carbon atoms, $R_5$ is methylene and Y is $Y_1$—B—$Y_2$ in which $Y_1$ is phenyl, B is single carbon—carbon bond or —CO—NH— and $Y_2$ is cyano, carboxy free or esterified by an alkyl of 1 to 4 carbon atoms, indolyl or phenyl optionally substituted by a free, salified or esterified carboxy, tetrazolyl, tetrazolylalkyl, tetrazolylcarbamoyl in which the tetrazolyl is optionally substituted by an alkyl, alkenyl or alkoxyalkyl or by —$(CH_2)_p$—$SO_2$—$X_a$—$R_{14a}$ in which p is 0 or 1, $X_a$ is —NH—, —NH—CO—NH, —NH—CO— or a single bond and $R_{14a}$ is methyl, ethyl, vinyl, allyl, pyridylmethyl, pyridylethyl, pyridyl, phenyl or benzyl, said products of formula I being in all possible racemic, enantiomeric and diastereoisomeric isomer forms, as well as the addition salts with mineral and organic acids or with mineral and organic bases of said products of formula I.

Another preferred group of compounds of the invention are those of formula

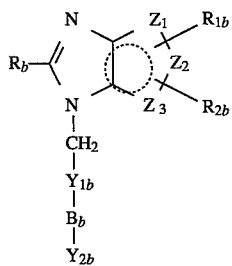  $I_b$ wherein $R_b$ is n-butyl or butenyl, $Z_1$, $Z_2$, $Z_3$ are such that one is sulfur and the other two are individually methine =CH—, $R_{1b}$ and $R_{2b}$ individually are selected from the group consisting of hydrogen; halogen, hydroxyl; mercapto, alkoxy of 1 to 6 carbon atoms; alkyl, alkenyl, alkynyl and alkylthio of up to 6 carbon atoms and the aryl, aralkyl or arylalkenyl in which the alkyl and alkenyl have at most 6 carbon atoms, the aryl, arylalkyl and arylalkenyl are a monocyclic containing 5 to 6 links or condensed ring containing 8 to 14 links optionally containing one or more heteroatoms chosen from oxygen, nitrogen or sulfur, all the alkyl, alkenyl, alkynyl, alkylthio, aryl, arylalkyl and arylalkenyl being optionally substituted by at least one member of the group consisting of halogen, hydroxyl, alkoxy or alkylthio of 1 to 4 carbon atoms, mercapto, acyl, acyloxy; free carboxy, carboxy esterified by alkyl of 1 to 4 carbon atoms, $Y_{1b}$ is phenyl, $B_b$ is a single bond or —CO—NH—, $Y_{2b}$ is such that if $B_b$ is a single bond or —CO—NH—, $Y_{2b}$ is phenyl optionally substituted by free, salified or esterified carboxy, tetrazolyl, tetrazolylmethyl, tetrazolylcarbamoyl, —$SO_2$—$X_b$—$R_{14b}$ in which $X_b$ is a single bond, or —NH—, —CO— and —NH—CO— and $R_{14b}$ is methyl, ethyl, vinyl, allyl, pyridylmethyl, pyridylethyl, pyridyl, phenyl or benzyl, or if $B_b$ is a single bond, $Y_{2b}$ is cyano or free, salified or esterified carboxy, said products of formula $I_b$ being in all possible racemic, enantiomeric and diastereoisomeric isomer forms, as well as the addition salts with mineral and organic acids or with mineral and organic bases of said products of formula $I_b$.

A more preferred group of compounds are those of the formula

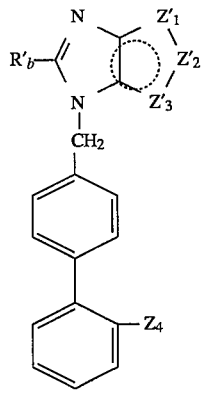

wherein $R'_b$ is n-butyl, $Z'_1$, $Z'_2$ and $Z'_3$ are such that: one is sulfur, and the other two individually are methine =CH— optionally substituted by 1 to 4 carbon atoms, and $Z_4$ is carboxy free, salified or esterified by alkyl of 1 to 4 carbon atoms or tetrazolyl, said products of formula $I'_b$ being in all possible racemic, enantiomeric or diastereoisomer isomer forms, as well as the addition salts with mineral and organic acids or with mineral and organic bases of said products of formula $I'_b$.

Among specific products of the invention are: 2-butyl-1-[(4-carboxyphenyl)-methyl]-1H-benzimidazole-6 -carboxylic acid, 4-[(2-butyl-1H-benzimidazol-1-yl)-methyl]-benzoic acid, 4-[(2-butyl-1 H-benzimidazol-1-yl)-methyl]-N-(1H-indol-4-yl)-benzamide, 4-[(2-butyl-1H-naphth-( 2,3-d)-imidazol-1-yl)-methyl]-benzoic acid, 4-[(2-butyl-5,6-dimethyl-1H-benzimidazol-1-yl)-methyl]-benzoic acid, 4-[(2-butyl-3H-imidazol-(4,5-c)-pyridin-3-yl)-methyl]-benzoic acid, 4'-((2-butyl-3H-imidazo-(4,5-b)-pyridin-3-yl)-methyl)-(1,1'-biphenyl)-2-carboxylic acid and 1,1-dimethylethyl 2-butyl-1-((2'-carboxy-(1,1'-biphenyl)-4-yl)-methyl)-6-hydroxy-1H-thieno-(2,3,-d)-imidazole-5-carboxylate and their addition salts with mineral and organic acids or with mineral and organic bases.

The process of the invention for the preparation of a compound of formula I comprises reacting a compound of the formula

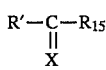 II wherein X is oxygen or =NH, $R_{15}$ is hydroxy or alkoxy or halogen or $NH_2$, and R' has the meaning indicated above for R in which the optional reactive functions are optionally protected by protector groups with a compound of the formula

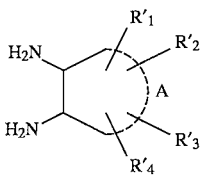

wherein $R_1$, $R_2$, $R_3$ and $R_4$ have the above meanings for $R_1$, $R_2$, $R_3$ and $R_4$ respectively in which the optional reactive functions are optionally protected by protector groups to obtain a product of formula IV, after optional isolation of an intermediate of formula

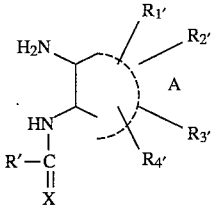

wherein $R'$, $R_1$, $R_2$, $R_3$ and $R_4$ have the above meanings which product of the formula

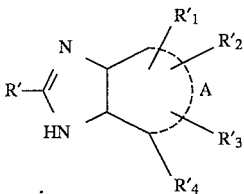

in which $R'$, $R_1$, $R_2$, $R_3$ and $R_4$ have the above meanings is reacted with a compound of the formula

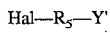

wherein Hal is halogen, $R_5$ has the above meaning and Y' has the above meaning for Y in which the optional reactive functions are optionally protected by protector groups to obtain a compound of the formula

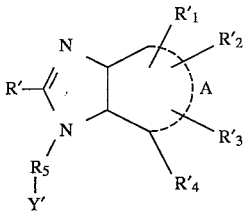

wherein $R'$, $R'_1$, $R'_2$, $R'_3$, $R'_4$, $R_5$ and Y' have the above meanings or a compound of the formula

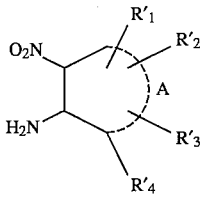

wherein $R'_1$, $R'_2$, $R'_3$ and $R'_4$ have the above meanings for $R_1$, $R_2$, $R_3$ and $R_4$ respectively in which the optional reactive functions are optionally protected by protector groups is reacted either with a compound of the formula

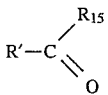

wherein I and $R_{15}$ have the above meanings to obtain the product of the formula

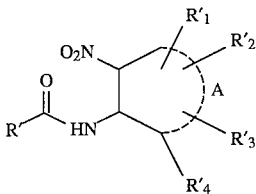

wherein $R'$, $R'_1$, $R'_2$, $R'_3$ and $R'_4$ have the previous meanings, which product of formula X either is reduced into a product of the formula

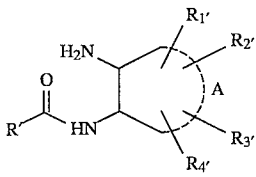

wherein $R'$, $R'_1$, $R'_2$, $R'_3$ and $R'_4$ have the previous meanings, which is cyclized into a product of formula IV as defined above which is treated is indicated above to obtain a product of formula IX or the product of formula X is reacted with the compound of formula X' as defined above to obtain a product of the formula

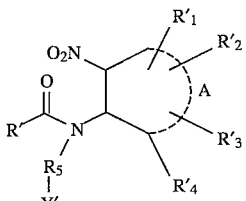

wherein $R'$, $R_1$, $R_2$, $R_3$, $R_4$, $R_5$ and Y' have the previous meanings which is subjected to a selective reduction of the nitro to obtain a product of the formula

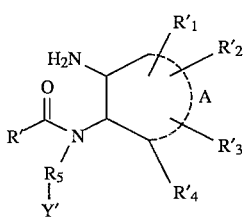

wherein $R'$, $R'_1$, $R'_2$, $R'_3$, $R'_4$, $R_5$ and Y' have the previous meanings which is subjected to a cyclization to obtain the products of formula IX as defined above, or the compound of formula VI is reacted with the compound of formula V as defined above to obtain a product of the formula

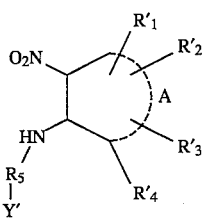

VII wherein R'₁, R'₂, R'₃, R'₄, R₅ and Y' have the meanings indicated above which either is reacted with a compound of formula II' as defined above to obtain a product of formula XI as defined above which is then treated as indicated above, or is subjected to a reduction of the nitro into the amino to obtain a product of the formula

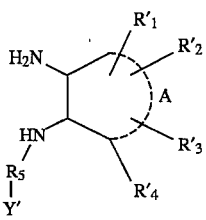

VIII in which R₁', R₂', R₃', R₄', R₅ and Y' have the meanings indicated above, which is reacted with a product of formula II as defined above to obtain a product of formula IX as defined above, which product of formula IX is treated, if desired and if necessary, to at least one of the following reactions in any order:

an elimination reaction of the protector groups that can be carried by the protected reactive functions, a salification reaction by a mineral or organic acid or by a base to obtain the corresponding salt, an esterification or salification reaction of the acid function, a saponification reaction of the ester function into an acid function, a conversion reaction of the alkoxy function into the hydroxyl function, a conversion reaction of the cyano function into an acid function, a reduction reaction of the carboxy function into an alcohol function, a substitution reaction of the hydroxyl or mercapto function by a halogen atom, a substitution reaction on an halogen atom, a resolution function of the racemic forms into resolved products, said products of formula I thus obtained being in all possible racemic, enantiomeric and diastereoisomeric isomer forms.

The products of formula IV may be obtained by the addition of the product of formula II on a free mine function of the product of formula III and cyclization on the second free amine function of the product thus formed. The product of formula IV can be obtained by the action of the compound of formula II with a compound of formula III under various reaction conditions, especially the compound of formula II can be condensed on the compound of formula III preferably in an organic solvent such as tetrahydrofuran or dimethylformamide at reflux or at a temperature of between approximately 20° C. and 200° C.

The compound of formula II can be, when X is =NH, ethyl pentanimidoate and when X is =O, valeric acid. The compound of formula II which can be such that X is oxygen and R₁₅ is hydroxyl and may be valeric acid and can also be put in the presence of the compound of formula III, which can be a derivative of pyridine at temperature of approximately 170° C. preferably with stirring for approximately 18 hours.

The products of formula IV can be condensed with a compound of formula V to obtain products of formula IX. The condensation reaction of products of formula IV with a compound of formula V in which the halogen is preferably a bromine can be carried out in an organic solvent such as dimethylformamide or tetrahydrofuran and the halogenated derivative can be condensed on the anion of the amidazole of formula IV prepared for example by the action of a strong base such as sodium or potassium hydride or also of a sodium or potassium alcoholate such as sodium methylate or potassium carbonate in dimethylformamide.

The addition reaction of the compound of formula II' on the free amine function of the compound of formula VI to obtain the products of formula X can be carried out by simple heating to a temperature of approximately 120° C. to 170° C. and the compound of formula II' can be valeric acid, then preferably used in excess relative to the compound of formula VI.

The addition reaction of the compound of formula V on the free amine function of the compound of formula X to obtain the products of formula XI can be carried out at ambient temperature or by heating to a temperature of approximately 20° C. to 150° C., preferably in the presence of a base such as triethylamine, sodium hydroxide, sodium methylate or ethylate or also sodium hydride in a solvent such as tetrahydrofuran or dimethylformamide.

The reduction of the nitro of the products of formula XI into an amino to obtain the products of formula XII as well as the reduction of the products of formula X into the products of formula X' can be carried out by the usual methods known to one skilled in the art, notably by catalytic hydrogenation in the presence palladium hydroxide in a solvent such as ethanol or by zinc in a solvent such as acetic acid in the presence of sodium acetate or by sodium borohydride.

The cyclization reaction of the product of formula XII to obtain the products of formula IX can be carried out by simple heating or in the presence of a catalyst such as thionyl chloride, phosphorous pentachloride or phosphoric anhydride in a solvent such as tetrahydrofuran or dimethylformamide.

The addition reaction of the compound of formula V on the free amine unction of the compound of formula VI to obtain the products of formula VII can be carried out under the same conditions as those described above for the addition of the compound of formula V on the products of formula IV. The reaction of the product of formula VII with the compound of formula II' is carried out under the same conditions as the reaction of the product of formula VI with the compound of formula II'.

The reduction of the nitro of the products of formula VII into an amino to obtain the products of formula VIII can be carried out by the usual methods known to one skilled in the art, notably under the same conditions as those described above for the reduction of the nitro of the products of formula XI into an amino to obtain the products of formula XII.

The addition reaction of the compound of formula II on the free amine of the products of formula VIII followed by the cyclization of the products can be carried out under the same conditions as those described above for the addition of the compound of formula II on the compound of formula III.

From what is indicated above, the products of formula IX can therefore be obtained either by the reaction of products of formula IV with a compound of formula V or by a cyclization reaction of the products of formula XII or by the reaction of the product of formula VIII with the compound of formula II.

Depending on the value of R, $R'_1$, $R'_2$, $R'_3$, $R'_4$ and Y', the products of formula IX either constitute or do not constitute the products of formula I.

The various reaction functions which can be carried out by some compounds of the reactions defined above can, if necessary, be protected for example, hydroxyl, acyl, free carboxy or amino and monoalkylamino can be protected with appropriate protective groups.

The following non exhaustive list of examples of the protection of reactive functions can be mentioned: hydroxyl can be protected by alkyl, trimethylsilyl, dihydropyranyl, methoxymethyl or tetrahydropyrannyl, amino can be protected by acetyl, trityl, benzyl, tert-butoxycarbonyl, phthalimido or other groups known in the chemistry of peptides, acyl such as formyl can be protected in the form of cyclic or non cyclic ketals such as dimethyl or diethylketal or ethylene dioxyketal; the acid functions of products can be optionally amidified by a primary or secondary amine in the presence of methylene chloride in 1-ethyl-3-(dimethylaminopropyl)carbodiimide hydrochloride at ambient temperature: the acid functions can be protected in the form of esters formed with easily cleavable esters such as benzyl or tert-butyl esters or esters known in the chemistry of peptides.

The elimination of these protective groups is carried out under the usual conditions known to one skilled in the art such as acid hydrolysis carried out with an acid such as hydrochloric acid, benzene sulfonic acid or p-toluene sulfonic acid or trifluoroacetic acid. The phthalimido group is eliminated by hydrazine. A list of the different useable protector groups will be found in U.S. Pat. No. 2,499,995.

The products described above can be subjected to salification reactions by a mineral or organic acid or a base by the usual methods known to one skilled in the art.

The products described above can also be subjected to salification reactions by a mineral or organic base or esterification reactions on the optional carboxy functions, these esterification and salification reactions can be carried out by the usual methods known to one skilled in the art. The optional esterified carboxy functions of the products can be reduced into an alcohol by methods known to one skilled in the art, preferably, with lithium aluminium hydride in a solvent such as tetrahydrofuran or dioxane or ethyl ether.

The optional conversions of ester functions into the acid function of the products described above can be carried out under the usual conditions known to one skilled in the art, such as acid or alkaline hydrolysis with sodium or potassium hydroxide in an alcoholic medium such as methanol or by sulfuric acid or hydrochloric acid.

The optional cyano functions of the products can be converted into an acid function under the usual conditions known to one skilled in the art for example, by a hydrolysis carried out in an acid medium such as in a mixture of sulfuric acid, glacial acetic acid and water, these three compounds being preferably in equal proportions, or also in a mixture of sodium hydroxide, ethanol and water at reflux.

The optional alkoxy functions such as methoxy of the products can be converted into an alcohol function under the usual conditions known to one skilled in the art by boron tribromide in a solvent such as methylene chloride, by pyridine hydrobromide or hydrochloride or by hydrobromic acid or hydrochloric acid in water or acetic acid at reflux.

The optional substitution reactions with halogen and substitution reactions of the hydroxyl or mercapto functions by halogen can be carried out under the usual conditions known to one skilled in the art such as with thionyl chloride, phosphorous pentachloride ($PCl_5$), phosphorous oxychloride ($POCl_3$) in a solvent such a ether, methylene chloride or tetrahydrofuran in the presence or not of a base such as pyridine, or by a methane tetrahalogen such as tetrachloride or tetrabromide and triphenylphosphine.

The possible optically active forms of the products of formula I can be prepared by resolution of the racemics by the usual methods.

A modification of the process of the invention to produce the products of the formula

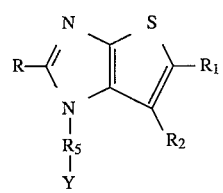

wherein R, $R_1$, $R_2$, $R_5$ and Y have the above meanings comprises either reacting a compound of the formula

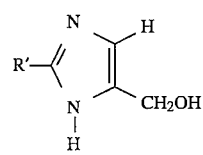

wherein R' has the above meaning for R in which the optional reactive functions are optionally protected with a halogenation agent to obtain a compound of the formula

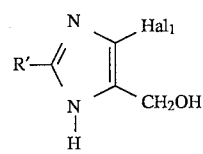

wherein R' has the above meaning and $Hal_1$ is halogen, preferably bromine, subjecting the latter to an oxidation reaction to obtain a compound of the formula

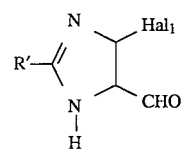

wherein R' and $Hal_1$ have the above meanings, reacting the latter with a compound of the formula

wherein Hal, $R_5$ and Y' have the above meanings to obtain a compound of the formula

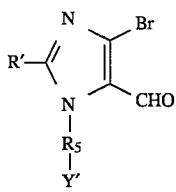

wherein R', R$_5$ and Y' have the above meanings, reacting the latter with a compound of the formula

wherein R'$_1$ has the above meaning for R$_1$ in which the optional reactive functions are optionally protected to obtain after cyclization a compound of the formula

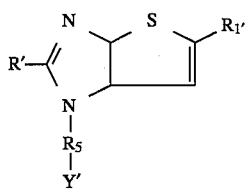

corresponding to the products of formula I$_c$ in which R$_2$ is hydrogen, or a compound of the formula

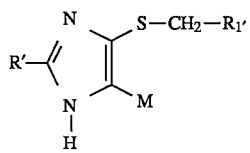

in which R' and R$_1$' have the meanings indicated above in which the optional reactive functions are optionally protected, and M is cyano or

in which R$_2$' has the meaning indicated above for R$_2$ in which the optional reactive functions are optionally protected and Z is oxygen or sulfur, is reacted with the compound of formula V to obtain the product of the formula

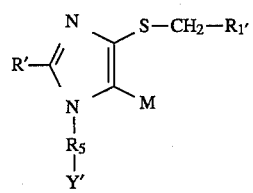

in which R', R$_1$', R$_5$ and Y' have the above meanings, subjecting the latter to a cyclization reaction to obtain a compound of the formula

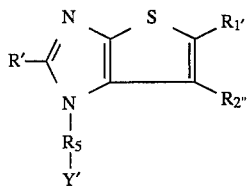

in which R', R$_1$', R$_5$ and Y' have the above meanings and R$_2$" has the meaning indicated above for R$_2$', which products of formula I$_c$' and I$_c$" are treated, if desired and if necessary, by at least one of the following reactions, in any order:

an elimination reaction of the protector groups that can be carried by the protected reactive functions, a salification reaction by a mineral or organic acid or by a base to obtain the corresponding salt, an esterification or salification reaction of the acid function, a saponification reaction of the ester function into an acid function, a conversion reaction of the alkoxy function into a hydroxyl function, a conversion reaction of the cyano function into an acid function, a reduction reaction of the carboxy function into an alcohol function, a substitution reaction of the hydroxyl or mercapto function by a halogen atom, a substitution reaction on a halogen atom, a resolution reaction of the racemic forms into resolved products, said products of formula I$_c$ thus obtained being in all possible racemic, enantiomeric and diastereoisomeric isomer forms.

The steps of the above process can be carried out by the usual methods known to one skilled in the art.

Preferably, the halogenation of the compound of formula XIII into the compound of formula XIV can be carried out by the usual methods known to one skilled in the art and in the presence of a halogenating agent such as N-bromo succinimide in a solvent such as dioxane or an alcohol such as ethanol or N-halo-succinimide in dioxane or as indicated for example in the Patent Application EP 0,253,310.

The oxidation reaction of the compound of formula XIV into the compound of formula XV being an alcohol function into an aldehyde function, can be carried out by the action of manganese dioxide in a solvent such as dioxane or dichloromethane or pyridinium chlorochromate or pyridinium dichromate, for example, in dichloromethane or dimethyl sulfoxide/oxalyl chloride in dichloromethane.

The addition reaction of the compound of formula V on the compound of formula XV to obtain a compound of formula XVI can be carried out as indicated above in the addition reaction of this compound of formula V with the compound of formula IV to obtain a product of formula IX, either in a solvent such as dimethylformamide in the presence of potassium or sodium bicarbonate or also sodium carbonate or potassium carbonate in dimethylformamide or dimethylsulfoxide, or sodium or potassium hydroxide in dimethylformamide, or an alkali metal alcoholate such as sodium or potassium methylate or ethylate in dimethylformamide or tetrahydrofuran, or for example as indicated in the European Application EP 0,253,310.

The addition reaction of the compound of formula XVII to the compound of formula XVI followed by cyclization to obtain a compound of formula $I_c'$ can be carried out in the presence of a sodium or potassium alcoholate such as sodium ethylate in a solvent such as an alcohol such as methanol or ethanol. The compounds of formula $I_c'$ correspond to the products of formula I which $R_2$ is hydrogen.

The addition reaction of the compound of formula V to the compound of formula XVIII to obtain a compound of formula XIX can be carried out under the same conditions as those indicated above for the addition of the compound of formula V to the compound of formula XV:

The cyclization reaction of the compound of formula XIX into the compound of formula $I_c''$ can be carried out in a solution of lithium or sodium (bis trimethylsilyl) amide, sodium or potassium hydride or also lithium diisopropyl amide in a solvent such as tetrahydrofuran, dimethylformamide or dimethoxyethane.

The compounds of formula $I_c''$ can represent all of the products of formula I as defined above when M in the compounds of formula XVIII is

as defined above

In the case where M in the compounds of formula XVIII is cyano, the products of formula $I_c''$ are obtained, representing the products of formula I in which $R_2$ is amino. This amino can be optionally substituted by the usual methods known to one skilled in the art into a derivative of the amino to obtain a product of formula I.

The products of formula $I_c'$ and $I_c''$ which are products of formula I can be subjected to one or more of the above indicated reactions which can be carried out in the usual conditions known to one skilled in the art such as under the conditions defined above for the products of formula IX.

The novel compositions of the invention having angiotensin II receptor antagonistic activity are comprised of an effective amount of at least one imidazole of formula I and their non-toxic, pharmaceutically acceptable salts with acids and bases and an inert pharmaceutical carrier. The compositions may be in the form of tablets, dragees, capsules, suppositories, injectable preparations, ointments, creams, gels and aerosol preparation.

Examples of suitable excipients are talc, arabic gum, lactose, starch, maganesium stearate, cocoa butter, aqueous or non-aqueous vehicles, fatty substances of animal or vegetable origin, paraffin derivatives, glycols, various wetting, dispersing or emulisfing agents and preservatives.

The compositions are endowed with antagonistic properties for the angiotensin II receptor and are therefot inhibitors of angiotensin II effects, especially of the vasoconstrictor effect and also the trophic effect at the level of the myocytes. The compositions are useful in the treatment of arterial hypertension, cardiac insufficiencies, renal insufficiencies and in the prevention of post-angipolastic recurrences of stenosis. They are also useful in the treatment of some gastro-intestinal, gynaecological disorders and especially for a relaxing effect at the level of the uterus.

The novel method of the invention for inducing angiotensin II receptor antagonistic activity in warm-blooded animals, including humans, comprising administering to warm-blooded animals an antagonistically effective amount to inhibit angiotensin II receptors of at least one imidazole of formula I and their non-toxic, pharmaceutcally acceptables salt with an acid or base. The compounds may be administered orally, rectally parenterally or topically to the skin or mucous membranes. The usual daily dose is 0.013 to 1.33 mg/kg depending on the method of administration, the specific compound and the condition treated.

The starting compounds of formulae II, II', III, V, VI, XIII, XVII and XVIII can be obtained commercially or can be prepared by methods known to one skilled in the art.

Some compounds of formula III can be found commercially such as methyl 3,4-diaminobenzoate which can be found in the form of a product which is available commercially from LANCASTER.

Numerous examples of the preparation of compounds of formula III are described in the literature and examples are: Bul. S.O.C. chim (1957), pp 2197–2201; Beil. 22, (2), 394; Beil. 22, (2), 395; Beil. 24, 324; Bei. 13, 270; Beil. 13, 207; Beil. 13, 179; Beil. 25, 481; Beil. 13, 1 and Beil. 24, 469.

Among the compounds of formula II and II' are valeric acid or ethyl pentanimidoate which can be prepared by action of gaseous hydrochloric acid in ethanol on valeronitrile which can be found in the form of a product commercially available from LONZA. An example of the preparation of these compounds of formula II is given in J.A.C.S. (1942), Vol. 64, pp. 1827.

A process for the preparation of certain products of formula V comprises subjecting the compound of the formula

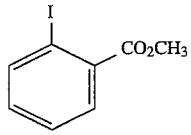

Va which is methyl iodobenzoate which can be found in the form of a product commercially available from JANSSEN to the action of a compound of the formula

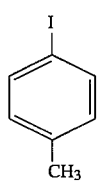

Vb which is iodotoluene which one can be found in the form of a product commercially available from FLUKA, the reaction being carried out in the presence of copper powder at a temperature of about 100° C. to 300° C. to obtain a product of the formula

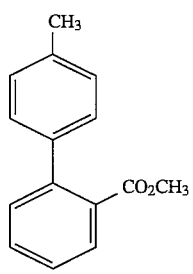

Vc the esterified carboxy which can be liberated from the alkyl by standard methods known to one skilled in the art or by acid or alkaline hydrolysis, which can be subjected to a bromination reaction on the methyl by standard methods known to one skilled in the art by the action of n-bromosuccinimide in carbon tetrachloride.

Examples of the preparation of compounds of formula V are described in the literature such as in U.S. Pat. No. 4,880,804 and in European Patent Application No. EP 0,400,974.

The compounds of formula VI can be orthonitroaniline which is known in the form of a product commercially available from UCB. Examples of the preparation of compounds of formula VI are described in the literature such as Canadian Journal of Chemistry, 1977, 55, (10), pp. 1653 to 1657, Beil. 22, (1), 631; Beil. 13, (2), 191 or Beil. 14, (1), 583. The compounds of formula XIII can be prepared as indicated in European Patent Application E 0,253,310.

Certain compounds of formula XVII can be found commercially such as methyl thioglycolate, benzylmercaptan or also n-butyl-mercaptan or thioacetal which can be found in the form of a product commercially available from ALDRICH.

Numerous examples of the preparation of compounds of formula XVII are described in the literature such as: ORGANICS SYNTHESIS COLL., VOL. 4, p. 296.

Finally, the novel intermediate products necessary for the preparation of products of formula are compounds of formula IV VII, VIII, XVI, XVIII and XIX, especially those wherein $R_a$, $X_4$, $X_5$, $X_6$, $X_7$, $R_{1a}$, $R_{2a}$, $Y_{1a}$, $B_a$ and $Y_{2a}$ are those of formula $I_a$.

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| nBu | —CH= | —CH= | —CH= | —CH= | H | OH | 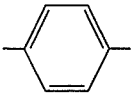 | — | COOH |
| " | " | " | " | " | OH in 4 | " | " | " | " |
| " | " | " | " | " | OH in 5 | " | " | " | " |
| " | " | " | " | " | OH in 6 | " | " | " | " |
| " | " | " | " | " | OH in 7 | " | " | " | " |
| " | " | " | " | " | CH$_2$OH in 4 | " | " | " | " |
| " | " | " | " | " | CH$_2$OH in 5 | " | " | " | " |
| " | " | " | " | " | CH$_2$OH in 6 | " | " | " | " |
| " | " | " | " | " | CH$_2$OH in 7 | " | " | " | " |
| " | " | " | " | " | COOH in 4 | " | " | " | " |
| " | " | " | " | " | COOH in 5 | " | " | " | " |
| " | " | " | " | " | COOH in 6 | " | " | " | " |
| " | " | " | " | " | COOH in 7 | " | " | " | " |
| " | " | " | " | " | COOMe in 4 | " | " | " | " |
| " | " | " | " | " | COOMe in 5 | " | " | " | " |
| " | " | " | " | " | COOMe in 6 | " | " | " | " |
| " | " | " | " | " | COOMe in 7 | " | " | " | " |
| " | " | " | " | " | CH$_3$ in 4 | " | " | " | " |
| nBu | —CH= | —CH= | —CH= | —CH= | CH$_3$ in 5 | OH | 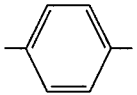 | — | COOH |
| " | " | " | " | " | CH$_3$ in 6 | " | " | " | " |
| " | " | " | " | " | CH$_3$ in 7 | " | " | " | " |
| " | " | " | " | " | CH$_2$OH in 6 | H | " | " | " |
| " | " | " | " | " | CH$_2$OH in 5 | " | " | " | " |
| " | " | " | " | " | OCH$_3$ in 6 | H | " | " | " |
| " | " | " | " | " | Cl in 6 | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | " | " | " | " | 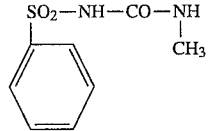 SO$_2$—NH—CO—NH—CH$_3$ |
| " | " | " | " | " | COOH in 6 | " | " | " | " |
| " | " | " | " | " | COOH in 5 | " | " | " | " |
| " | " | " | " | " | CH$_2$OH in 6 | " | " | " | " |
| " | " | " | " | " | CH$_2$OH in 5 | " | " | " | " |
| " | " | " | " | " | OH in 6 | " | " | " | " |
| " | " | " | " | " | OH in 5 | " | " | " | " |
| " | " | " | " | " | CO$_2$CH$_3$ in 6 | " | " | " | " |
| " | " | " | " | " | CO$_2$CH$_5$ in 5 | " | " | " | " |
| " | " | " | " | " | Cl in 6 | " | " | " | " |
| " | " | " | " | " | COOH in 6 | " | " | " | 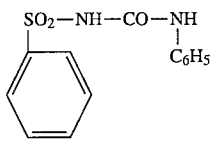 SO$_2$—NH—CO—NH—C$_6$H$_5$ |
| " | " | " | " | " | COOH in 5 | " | " | " | " |
| " | " | " | " | " | CH$_2$OH in 6 | H | " | " | " |
| " | " | " | " | " | CH$_2$OH in 5 | " | " | " | " |
| " | " | " | " | " | OH in 5 | H | " | " | " |
| " | " | " | " | " | OH in 6 | H | " | " | " |
| " | " | " | " | " | CO$_2$CH$_3$ in 6 | " | " | " | " |
| " | " | " | " | " | CO$_2$CH$_3$ in 5 | " | " | " | " |
| " | " | " | " | " | Cl in 3 | " | " | " | " |
| " | " | " | " | " | COOH in 3 | " | " | " | 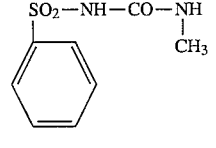 SO$_2$—NH—CO—NH—CH$_3$ |
| " | " | " | " | " | COOH in 4 | " | " | " | " |
| " | " | " | " | " | CH$_2$OH in 3 | " | " | " | " |
| " | " | " | " | " | CH$_2$OH in 4 | " | " | " | " |
| " | " | " | " | " | OH in 3 | " | " | " | " |
| " | " | " | " | " | OH in 4 | " | " | " | " |
| " | " | " | " | " | CO$_2$CH$_3$ in 3 | " | " | " | " |
| " | " | " | " | " | CO$_2$CH$_3$ in 4 | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | Cl in 3 | " | " | " | 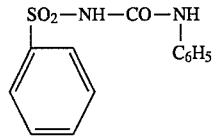 SO₂—NH—CO—NH—C₆H₅ |
| " | " | " | " | " | COOH in 3 | " | " | " | " |
| " | " | " | " | " | COOH in 4 | " | " | " | " |
| " | " | " | " | " | CH₂OH in 3 | " | " | " | " |
| " | " | " | " | " | CH₂OH in 4 | " | " | " | " |
| " | " | " | " | " | OH in 3 | " | " | " | " |
| " | " | " | " | " | OH in 4 | " | " | " | " |
| " | " | " | " | " | CO₂CH₃ in 3 | " | " | " | " |
| " | " | " | " | " | CO₂CH₃ in 4 | " | " | " | " |
| nbu | N | —CH= | —CH= | —CH= | H | H | " | " | COOH |
| " | " | " | " | " | CH₂OH in 7 | " | " | " | " |
| " | " | " | " | " | CH₂OH in 5 | " | " | " | " |
| " | " | " | " | " | COOH in 7 | " | " | " | " |
| " | " | " | " | " | CH₂OH in 6 | " | " | " | " |
| " | " | " | " | " | CO₂CH₃ in 6 | " | " | " | " |
| " | " | " | " | " | CH₂OCH₃ in 6 | " | " | " | " |
| " | " | " | " | " | COOH in 6 | " | " | " | " |
| " | " | " | " | " | COOH in 5 | " | " | " | " |
| " | " | " | " | " | CO₂CH₃ in 7 | " | " | " | " |
| " | " | " | " | " | CH₂OCH₃ in 7 | " | " | " | " |
| nBu | N | —CH= | —CH= | —CH= | H | H |  | — | 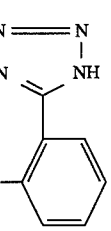 COOH |
| " | " | " | " | " | CH₂OH in 7 | " | " | " | " |
| " | " | " | " | " | CH₂OH in 5 | " | " | " | " |
| " | " | " | " | " | COOH in 7 | " | " | " | " |
| " | " | " | " | " | CH₂OH in 6 | " | " | " | " |
| " | " | " | " | " | CO₂CH₃ in 6 | " | " | " | " |
| " | " | " | " | " | CH₂OCH₃ in 6 | " | " | " | " |
| " | " | " | " | " | COOH in 6 | " | " | " | " |
| " | " | " | " | " | H | H | " | " | tetrazole-phenyl |

-continued

| $R_n$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | $CH_2OH$ in 7 | " | " | " | " |
| " | " | " | " | " | $CH_2OH$ in 5 | " | " | " | " |
| " | " | " | " | " | COOH in 7 | " | " | " | " |
| " | " | " | " | " | $CH_2OH$ in 6 | " | " | " | " |
| " | " | " | " | " | $CH_2CH_3$ in 6 | " | " | " | " |
| nBu | N | —CH= | —CH= | —CH= | $CO_2CH_3$ in 7 | H | — | | |
| " | " | " | " | " | $CH_2OCH_3$ in 7 | " | " | " | " |
| " | " | " | " | " | $CH_2OCH_3$ in 6 | " | " | " | " |
| " | " | " | " | " | COOH in 6 | " | " | " | " |
| nBu | —CH= | —CH= | N | —CH= | H | H | " | " | COOH |
| " | " | " | " | " | COOH in 5 | " | " | " | " |
| " | " | " | " | " | $CO_2CH_3$ in 5 | " | " | " | " |
| " | " | " | " | " | $CH_2OH$ in 5 | " | " | " | " |
| " | " | " | " | " | $CH_2OCH_3$ in 5 | " | " | " | " |
| " | " | " | " | " | $CH_2OH$ in 4 | " | " | " | " |
| " | " | " | " | " | COOH in 7 | " | " | " | " |
| " | " | " | " | " | $CO_2CH_3$ in 7 | " | " | " | " |
| " | " | " | " | " | $CH_2OH$ in 7 | " | " | " | " |
| " | " | " | " | " | $CH_2OCH_3$ in 7 | " | " | " | " |
| " | " | " | " | " | H | H | " | " | 2-COOH-C$_6$H$_4$— |
| nBu | —CH= | —CH= | N | —CH= | COOH in 5 | H | — | | 2-COOH-C$_6$H$_4$— |
| " | " | " | " | " | $CO_2CH_3$ in 5 | " | " | " | " |
| " | " | " | " | " | $CH_2OH$ in 5 | " | " | " | " |
| " | " | " | " | " | $CH_2OCH_3$ in 5 | " | " | " | " |
| " | " | " | " | " | $CH_2OH$ in 4 | " | " | " | " |
| " | " | " | " | " | COOH in 7 | " | " | " | " |
| " | " | " | " | " | $CO_2CH_3$ in 7 | " | " | " | " |
| " | " | " | " | " | $CH_2OH$ in 7 | " | " | " | " |
| " | " | " | " | " | $CH_2OCH_3$ in 7 | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| nBu | —CH= | —CH= | N | —CH= | H | H | ⟨phenylene⟩ | — | 3-(2-methylphenyl)-1H-1,2,4-triazole |
| " | " | " | " | " | COOH in 5 | " | " | " | " |
| " | " | " | " | " | $CO_2CH_3$ in 5 | " | " | " | " |
| " | " | " | " | " | $CH_2OH$ in 5 | " | " | " | " |
| " | " | " | " | " | $CH_2OCH_3$ in 5 | " | " | " | " |
| " | " | " | " | " | $CH_2OH$ in 4 | " | " | " | " |
| " | " | " | " | " | COOH in 7 | " | " | " | " |
| " | " | " | " | " | $CO_2CH_3$ in 7 | " | " | " | " |
| " | " | " | " | " | $CH_2OH$ in 7 | " | " | " | " |
| " | " | " | " | " | $CH_2OCH_3$ in 7 | " | " | " | " |
| " | " | " | " | " | COOH in 4 | " | " | " | 2-methylphenyl-$SO_2$—NH—CO—NH—$CH_3$ |
| " | " | " | " | " | COOH in 5 | " | " | " | " |
| " | " | " | " | " | $CH_2OH$ in 4 | " | " | " | " |
| " | " | " | " | " | $CH_2OH$ in 5 | " | " | " | " |
| " | " | " | " | " | OH in 4 | " | " | " | " |
| " | " | " | " | " | OH in 5 | " | " | " | " |
| " | " | " | " | " | $CH_2CH_3$ in 4 | " | " | " | " |
| " | " | " | " | " | $CO_2CH_3$ in 5 | " | " | " | " |
| " | " | " | " | " | COOH in 4 | " | " | " | 2-methylphenyl-$SO_2$—NH—CO—NH—$C_6H_5$ |
| " | " | " | " | " | COOH in 5 | " | " | " | " |
| " | " | " | " | " | $CH_2OH$ in 4 | " | " | " | " |
| " | " | " | " | " | $CH_2OH$ in 5 | " | " | " | " |
| " | " | " | " | " | OH in 4 | " | " | " | " |
| " | " | " | " | " | OH in 5 | " | " | " | " |
| " | " | " | " | " | $CO_2CH_3$ in 4 | " | " | " | 2-methylphenyl-$SO_2$—NH—CO—NH—$CH_3$ |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | $CO_2CH_3$ in 5 | " | " | " | " |
| " | " | " | " | " | COOH in 7 | " | " | " | " |
| " | " | " | " | " | $CH_2OH$ in 7 | " | " | " | " |
| " | " | " | " | " | OH in 7 | " | " | " | " |
| " | " | " | " | " | $CO_2CH_3$ in 7 | " | " | " | 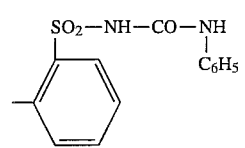 $SO_2-NH-CO-NH \atop C_6H_5$ |
| " | " | " | " | " | COOH in 7 | " | " | " | " |
| " | " | " | " | " | $CH_2OH$ in 7 | " | " | " | " |
| " | " | " | " | " | OH in 7 | " | " | " | " |
| " | " | " | " | " | $CO_2CH_3$ in 7 | " | " | " | " |
| nBu | $-CH=$ | $-CH=$ | $-CH=$ | N | H | H | H | " | COOH |
| " | " | " | " | " | $CH_2OH$ in 6 | " | " | " | " |
| " | " | " | " | " | COOH in 6 | " | " | " | " |
| " | " | " | " | " | $CH_2OCH_3$ in 6 | " | " | " | " |
| " | " | " | " | " | $CO_2CH_3$ in 6 | " | " | " | " |
| " | " | " | " | " | $CH_2OH$ in 5 | " | " | " | " |
| " | " | " | " | " | COOH in 5 | " | " | " | " |
| " | " | " | " | " | $CH_2OCH_3$ in 5 | " | " | " | " |
| " | " | " | " | " | $CO_2CH_3$ in 5 | " | " | " | " |
| nBu | $-CH=$ | $-CH=$ | $-CH=$ | N | H | H | 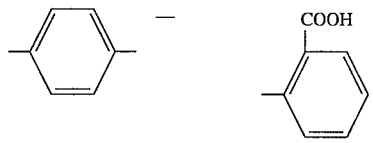 | — | 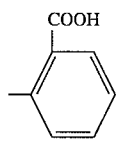 COOH |
| " | " | " | " | " | $CH_2OH$ in 6 | " | " | " | " |
| " | " | " | " | " | COOH in 6 | " | " | " | " |
| " | " | " | " | " | $CH_2OCH_3$ in 6 | " | " | " | " |
| " | " | " | " | " | $CO_2CH_3$ in 6 | " | " | " | " |
| " | " | " | " | " | $CH_2OH$ in 5 | " | " | " | " |
| " | " | " | " | " | COOH in 5 | " | " | " | " |
| " | " | " | " | " | $CH_2OCH_3$ in 5 | " | " | " | " |
| " | " | " | " | " | $CO_2CH_3$ in 5 | " | " | " | " |
| " | " | " | " | " | H | H | " | " | 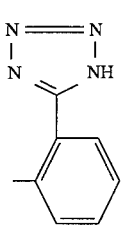 |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | CH₂OH in 6 | " | " | " | " |
| " | " | " | " | " | COOH in 6 | " | " | " | " |
| " | " | " | " | " | CH₂OCH₃ in 6 | " | " | " | " |
| " | " | " | " | " | CO₂CH₃ in 6 | " | " | " | " |
| nBu | —CH= | —CH= | —CH= | N | CH₂OH in 5 | H | ⟨C₆H₄⟩ | — | tetrazole-phenyl |
| " | " | " | " | " | COOH in 5 | " | " | " | " |
| " | " | " | " | " | CH₂OCH₃ in 5 | " | " | " | " |
| " | " | " | " | " | CO₂CH₃ in 5 | " | " | " | " |
| nBu | —CH= | N | —CH= | —CH= | H | H | " | " | COOH |
| " | " | " | " | " | COOH in 6 | " | " | " | " |
| " | " | " | " | " | CO₂CH₃ in 6 | " | " | " | " |
| " | " | " | " | " | CH₂OH in 6 | " | " | " | " |
| " | " | " | " | " | CH₂OCH₃ in 6 | " | " | " | " |
| " | " | " | " | " | CH₂OH in 4 | " | " | " | " |
| " | " | " | " | " | CH₂OH in 7 | " | " | " | " |
| " | " | " | " | " | COOH in 7 | " | " | " | " |
| " | " | " | " | " | CH₂OCH₃ in 7 | " | " | " | " |
| " | " | " | " | " | CO₂CH₃ in 7 | " | " | " | " |
| nBu | —CH= | N | —CH= | —CH= | H | H | ⟨C₆H₄⟩ | — | 2-COOH-phenyl |
| " | " | " | " | " | COOH in 6 | " | " | " | " |
| " | " | " | " | " | CO₂CH₃ in 6 | " | " | " | " |
| " | " | " | " | " | CH₂OH in 6 | " | " | " | " |
| " | " | " | " | " | CH₂OCH₃ in 6 | " | " | " | " |
| " | " | " | " | " | CH₂OH in 4 | " | " | " | " |
| " | " | " | " | " | CH₂OH in 7 | " | " | " | " |
| " | " | " | " | " | COOH in 7 | " | " | " | " |
| " | " | " | " | " | CH₂OCH₃ in 7 | " | " | " | " |
| " | " | " | " | " | CO₂CH₃ in 7 | " | " | " | " |

-continued

| Ra | X4 | X5 | X6 | X7 | R1a | R2a | Y1a | Ba | Y2a |
|---|---|---|---|---|---|---|---|---|---|
| " | " | " | " | " | H | H | " | " | tetrazole-substituted phenyl |
| " | " | " | " | " | COOH in 6 | " | " | " | " |
| " | " | " | " | " | CO₂CH₃ in 6 | " | " | " | " |
| " | " | " | " | " | CH₂OH in 6 | " | " | " | " |
| " | " | " | " | " | CH₂OCH₃ in 6 | " | " | " | " |
| nBu | —CH= | N | —CH= | —CH= | CH₂OH in 4 | H | para-phenylene | — | tetrazole-substituted phenyl |
| " | " | " | " | " | CH₂OH in 7 | " | " | " | " |
| " | " | " | " | " | COOH in 7 | " | " | " | " |
| " | " | " | " | " | CH₂OCH₃ in 7 | " | " | " | " |
| " | " | " | " | " | CO₂CH₃ in 7 | " | " | " | " |
| nBu | N | —CH= | N | —CH= | H | H | " | " | COOH |
| " | " | " | " | " | OH in 7 | " | " | " | " |
| " | " | " | " | " | OH in 5 | " | " | " | " |
| " | " | " | " | " | H | H | " | " | COOH-substituted phenyl |
| " | " | " | " | " | OH in 7 | " | " | " | " |
| " | " | " | " | " | OH in 5 | " | " | " | " |
| " | " | " | " | " | H | H | " | " | tetrazole-substituted phenyl |
| " | " | " | " | " | OH in 7 | " | " | " | " |
| " | " | " | " | " | OH in 5 | " | " | " | " |
| " | " | " | " | " | COOH in 7 | " | " | " | " |
| " | " | " | " | " | CH₂OH in 7 | " | " | " | " |
| nBu | —CH= | N | —CH= | N | H | H | para-phenylene | — | COOH |
| " | " | " | " | " | OH in 4 | H | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | OH in 4 | OH in 6 | " | " | " |
| " | " | " | " | " | H | H | " | " | ![2-COOH-phenyl] |
| " | " | " | " | " | OH in 4 | H | " | " | " |
| " | " | " | " | " | OH in 4 | OH in 6 | " | " | " |
| " | " | " | " | " | H | H | " | " | ![tetrazolyl-phenyl] |
| " | " | " | " | " | OH in 4 | H | " | " | " |
| " | " | " | " | " | OH in 4 | OH in 6 | " | " | " |
| nBu | —CH= | N | N | —CH= | H | H | " | " | COOH |
| " | " | " | " | " | OH in 4 | " | " | " | " |
| " | " | " | " | " | CH$_2$OH in 4 | " | " | " | " |
| " | " | " | " | " | COOH in 4 | " | " | " | " |
| " | " | " | " | " | CO$_2$CH$_3$ in 4 | " | " | " | " |
| " | " | " | " | " | OH in 7 | " | " | " | " |
| " | " | " | " | " | CH$_2$OH in 7 | " | " | " | " |
| " | " | " | " | " | COOH in 7 | " | " | " | " |
| " | " | " | " | " | CO$_2$CH$_3$ in 7 | " | " | " | " |
| nBu | —CH= | N | N | —CH= | H | H | ![p-phenylene] | — | ![2-COOH-phenyl] |
| " | " | " | " | " | OH in 4 | " | " | " | " |
| " | " | " | " | " | CH$_2$OH in 4 | " | " | " | " |
| " | " | " | " | " | COOH in 4 | " | " | " | " |
| " | " | " | " | " | CO$_2$CH$_3$ in 4 | " | " | " | " |
| " | " | " | " | " | OH in 7 | " | " | " | " |
| " | " | " | " | " | CH$_2$OH in 7 | " | " | " | " |
| " | " | " | " | " | COOH in 7 | " | " | " | " |
| " | " | " | " | " | CO$_2$CH$_3$ in 7 | " | " | " | " |
| " | " | " | " | " | H | H | " | " | ![tetrazolyl-phenyl] |
| " | " | " | " | " | OH in 4 | " | " | " | " |
| " | " | " | " | " | CH$_2$OH in 4 | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | COOH in 4 | " | " | " | " |
| " | " | " | " | " | CO₂CH₃ in 4 | " | " | " | " |
| " | " | " | " | " | OH in 7 | " | " | " | " |
| " | " | " | " | " | CH₂OH in 7 | " | " | " | " |
| " | " | " | " | " | COOH in 7 | " | " | " | " |
| " | " | " | " | " | CO₂CH₃ in 7 | " | " | " | " |
| nBu | N | N | —CH= | —CH= | H | H | *p-phenylene* | — | COOH |
| " | " | " | " | " | OH in 6 | " | " | " | " |
| " | " | " | " | " | CH₂OH in 6 | " | " | " | " |
| " | " | " | " | " | COOH in 6 | " | " | " | " |
| " | " | " | " | " | CO₂CH₃ in 6 | " | " | " | " |
| " | " | " | " | " | OH in 7 | " | " | " | " |
| " | " | " | " | " | CH₂OH in 7 | " | " | " | " |
| " | " | " | " | " | COOH in 7 | " | — | " | " |
| " | " | " | " | " | CO₂CH₃ in 7 | " | " | " | " |
| " | " | " | " | " | H | H | " | " | *o-COOH-phenyl* |
| " | " | " | " | " | OH in 6 | " | " | " | " |
| " | " | " | " | " | CH₂OH in 6 | " | " | " | " |
| " | " | " | " | " | COOH in 6 | " | " | " | " |
| " | " | " | " | " | CO₂CH₃ in 6 | " | " | " | " |
| " | " | " | " | " | OH in 7 | " | " | " | " |
| " | " | " | " | " | CH₂OH in 7 | " | " | " | " |
| " | " | " | " | " | COOH in 7 | " | " | " | " |
| " | " | " | " | " | CO₂CH₃ in 7 | " | " | " | " |
| nBu | N | N | —CH= | —CH= | H | H | *p-phenylene* | — | *o-(tetrazol-5-yl)phenyl* |
| " | " | " | " | " | OH in 6 | " | " | " | " |
| " | " | " | " | " | CH₂OH in 6 | " | " | " | " |
| " | " | " | " | " | COOH in 6 | " | " | " | " |
| " | " | " | " | " | CO₂CH₃ in 6 | " | " | " | " |
| " | " | " | " | " | OH in 7 | " | " | " | " |
| " | " | " | " | " | CH₂OH in 7 | " | " | " | " |
| " | " | " | " | " | COOH in 7 | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | $CO_2CH_3$ in 7 | " | " | " | " |
| nBu | —CH= | —CH= | N | N | H | H | " | " | COOH |
| " | " | " | " | " | OH in 4 | " | " | " | " |
| " | " | " | " | " | $CH_2OH$ in 4 | " | " | " | " |
| " | " | " | " | " | COOH in 4 | " | " | " | " |
| " | " | " | " | " | $CO_2CH_3$ in 4 | " | " | " | " |
| " | " | " | " | " | OH in 5 | " | " | " | " |
| " | " | " | " | " | $CH_2OH$ in 5 | " | " | " | " |
| nBu | —CH= | —CH= | N | N | COOH in 5 | H | 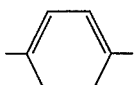 | — | COOH |
| " | " | " | " | " | $CO_2CH_3$ in 5 | " | " | " | " |
| " | " | " | " | " | H | H | " | " | 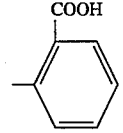 |
| " | " | " | " | " | OH in 4 | " | " | " | " |
| " | " | " | " | " | $CH_2OH$ in 4 | " | " | " | " |
| " | " | " | " | " | COOH in 4 | " | " | " | " |
| " | " | " | " | " | $CO_2CH_3$ in 4 | " | " | " | " |
| " | " | " | " | " | OH in 5 | " | " | " | " |
| " | " | " | " | " | $CH_2OH$ in 5 | " | " | " | " |
| " | " | " | " | " | COOH in 5 | " | " | " | " |
| " | " | " | " | " | $CO_2CH_3$ in 5 | " | " | " | " |
| " | " | " | " | " | H | H | " | " | 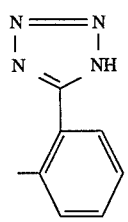 |
| " | " | " | " | " | OH in 4 | " | " | " | " |
| " | " | " | " | " | $CH_2OH$ in 4 | " | " | " | " |
| " | " | " | " | " | COOH in 4 | " | " | " | " |
| nBu | —CH= | —CH= | N | N | $CO_2CH_3$ in 4 | H | 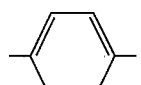 | — | 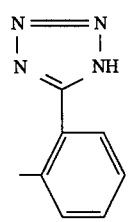 |
| " | " | " | " | " | OH in 5 | " | " | " | " |
| " | " | " | " | " | $CH_2OH$ in 5 | " | " | " | " |
| " | " | " | " | " | COOH in 5 | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | $CO_2CH_3$ in 5 | " | " | " | 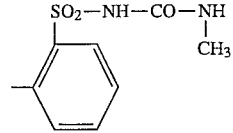 |
| " | " | " | " | " | COOH in 4 | " | " | " | " |
| " | " | " | " | " | COOH in 5 | " | " | " | " |
| " | " | " | " | " | $CH_2OH$ in 4 | " | " | " | " |
| " | " | " | " | " | $CH_2OH$ in 5 | " | " | " | " |
| " | " | " | " | " | OH in 4 | " | " | " | " |
| " | " | " | " | " | OH in 5 | " | " | " | " |
| " | " | " | " | " | $CO_2CH_3$ in 4 | " | " | " | " |
| " | " | " | " | " | $CO_2CH_3$ in 5 | " | " | " | 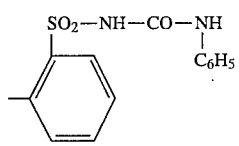 |
| " | " | " | " | " | COOH in 4 | " | " | " | " |
| nBu | —CH= | —CH= | N | N | COOH in 5 | H | " | — | 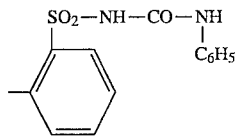 |
| " | " | " | " | " | $CH_2OH$ in 4 | " | " | " | " |
| " | " | " | " | " | $CH_2OH$ in 5 | " | " | " | " |
| " | " | " | " | " | OH in 4 | " | " | " | " |
| " | " | " | " | " | OH in 5 | " | " | " | " |
| " | " | " | " | " | $CO_2CH_3$ in 4 | " | " | " | " |
| " | " | " | " | " | $CO_2CH_3$ in 5 | " | " | " | " |
| nBu | N | —CH= | —CH= | N | H | H | " | " | COOH |
| " | " | " | " | " | OH in 5 | " | " | " | " |
| " | " | " | " | " | $CH_2OH$ in 5 | " | " | " | " |
| " | " | " | " | " | COOH in 5 | " | " | " | " |
| " | " | " | " | " | $CO_2CH_3$ in 5 | " | " | " | " |
| " | " | " | " | " | OH in 6 | " | " | " | " |
| " | " | " | " | " | $CH_2OH$ in 6 | " | " | " | " |
| " | " | " | " | " | COOH in 6 | " | " | " | " |
| " | " | " | " | " | $CO_2CH_3$ in 6 | " | " | " | " |
| " | " | " | " | " | H | H | " | " | 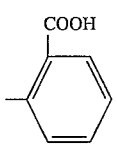 |
| " | " | " | " | " | OH in 5 | " | " | " | " |
| " | " | " | " | " | $CH_2OH$ in 5 | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| nBu | N | —CH= | —CH= | N | COOH in 5 | H | 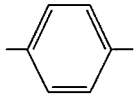 | — | 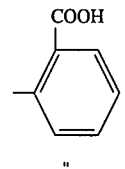 COOH |
| " | " | " | " | " | $CO_2CH_3$ in 5 | " | " | " | " |
| " | " | " | " | " | OH in 6 | " | " | " | " |
| " | " | " | " | " | $CH_2OH$ in 6 | " | " | " | " |
| " | " | " | " | " | COOH in 6 | " | " | " | " |
| " | " | " | " | " | $CO_2CH_3$ in 6 | " | " | " | " |
| " | " | " | " | " | H | H | " | " | 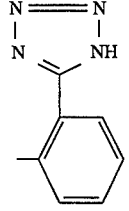 |
| " | " | " | " | " | OH in 5 | " | " | " | " |
| " | " | " | " | " | $CH_2OH$ in 5 | " | " | " | " |
| " | " | " | " | " | COOH in 5 | " | " | " | " |
| " | " | " | " | " | $CO_2CH_3$ in 5 | " | " | " | " |
| " | " | " | " | " | OH in 6 | " | " | " | " |
| " | " | " | " | " | $CH_2OH$ in 6 | " | " | " | " |
| " | " | " | " | " | COOH in 6 | " | " | " | " |
| " | " | " | " | " | $CO_2CH_3$ in 6 | " | " | " | " |
| nBu | N | —CH= | —CH= | N | H | H | 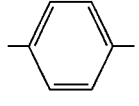 | — | $SO_2$—NH—CO—NH<br>\|<br>$CH_3$ |
| " | " | " | " | " | COOH in 6 | " | " | " | " |
| " | " | " | " | " | COOH in 5 | " | " | " | " |
| " | " | " | " | " | $CH_2OH$ in 6 | " | " | " | " |
| " | " | " | " | " | $CH_2OH$ in 5 | " | " | " | " |
| " | " | " | " | " | OH in 6 | " | " | " | " |
| " | " | " | " | " | OH in 5 | " | " | " | " |
| " | " | " | " | " | $CO_2CH_3$ in 6 | " | " | " | " |
| " | " | " | " | " | $CO_2CH_3$ in 5 | " | " | " | " |
| | | | | | | | | | 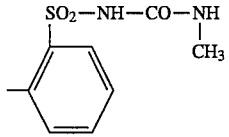 $SO_2$—NH—CO—NH<br>\|<br>$C_6H_5$ |
| " | " | " | " | " | COOH in 6 | " | " | " | " |
| " | " | " | " | " | COOH | " | " | " | " |

-continued

| $R_a$ | $X_4$ | $X_5$ | $X_6$ | $X_7$ | $R_{1a}$ | $R_{2a}$ | $Y_{1a}$ | $B_a$ | $Y_{2a}$ |
|---|---|---|---|---|---|---|---|---|---|
| " | " | " | " | " | $CH_2OH$ in 5 | " | " | " | " |
| " | " | " | " | " | $CH_2OH$ in 6 | " | " | " | " |
| " | " | " | " | " | OH in 6 | " | " | " | " |
| " | " | " | " | " | OH in 5 | " | " | " | " |
| " | " | " | " | " | $CO_2CH_3$ in 6 | " | " | " | " |
| " | " | " | " | " | $CO_2CH_3$ in 5 | " | " | " | " |

In addition to the products described in the examples which illustrate the invention without however limiting it, and the products indicated in the above tables corresponding to formula ($I_a$), the following products constitute products which can be obtained within the scope of the present invention: the substituents $R_b$, $Z_1$, $Z_2$, $Z_3$, $R_{1b}$, $R_{2b}$, $Y_{1b}$, $B_b$ and $Y_{2b}$ are those indicated in formula ($I_b$).

| $R_b$ | $Z_1$ | $Z_2$ | $Z_3$ | $R_{1b}$ | $R_{2b}$ | $Y_{1b}$ | $B_b$ | $Y_{2b}$ |
|---|---|---|---|---|---|---|---|---|
| nBu | S | —CH= | —CH= | H | H | 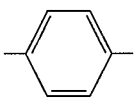 | — | 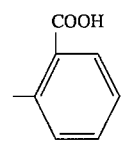 COOH |
| " | " | " | " | $CH_2OH$ in 5 | " | " | " | " |
| " | " | " | " | COOH in 5 | " | " | " | " |
| " | " | " | " | $CH_2OH$ in 6 | " | " | " | " |
| " | " | " | " | $CO_2CH_3$ in 6 | " | " | " | " |
| " | " | " | " | $CH_2OCH_3$ in 6 | " | " | " | " |
| " | " | " | " | COOH in 6 | " | " | " | " |
| " | " | " | " | $CO_2CH_3$ in 5 | " | " | " | " |
| " | " | " | " | OH in 6 | " | " | " | " |
| " | " | " | " | OH in 5 | " | " | " | " |
| " | " | " | " | H | H | " | — | COOH |
| " | " | " | " | $CH_2OH$ in 5 | " | " | " | " |
| " | " | " | " | COOH in 5 | " | " | " | " |
| " | " | " | " | $CH_2OH$ in 6 | " | " | " | " |
| " | " | " | " | $CO_2CH_3$ in 6 | " | " | " | " |
| " | " | " | " | $CH_2OCH_3$ in 6 | " | " | " | " |
| " | " | " | " | COOH in 6 | " | " | " | " |
| " | " | " | " | $CO_2CH_3$ in 6 | " | " | " | " |
| " | " | " | " | $CO_2CH_3$ in 5 | " | " | " | " |
| " | " | " | " | OH in 6 | " | " | " | " |
| " | " | " | " | OH in 5 | " | " | " | " |

-continued

| $R_b$ | $Z_1$ | $Z_2$ | $Z_3$ | $R_{1b}$ | $R_{2b}$ | $Y_{1b}$ | $B_b$ | $Y_{2b}$ |
|---|---|---|---|---|---|---|---|---|
| nBu | S | —CH= | —CH= | CH₂OCH₃ in 6 | H | | — | 2-(1H-tetrazol-5-yl)phenyl |
| " | " | " | " | COOH in 6 | " | " | " | " |
| " | " | " | " | H | H | " | " | " |
| " | " | " | " | OH in 5 | " | " | " | " |
| " | " | " | " | CO₂CH₃ in 5 | " | " | " | " |
| " | " | " | " | OH in 6 | " | " | " | " |
| " | " | " | " | CH₂OH in 5 | " | " | " | " |
| " | " | " | " | COOH in 5 | " | " | " | " |
| " | " | " | " | CH₂OH in 6 | " | " | " | " |
| " | " | " | " | CO₂CH₃ in 6 | " | " | " | 2-(SO₂—NH—CO—NH—CH₃)phenyl |
| " | " | " | " | COOH in 6 | " | " | " | " |
| " | " | " | " | COOH in 5 | " | " | " | " |
| " | " | " | " | CH₂OH in 6 | " | " | " | " |
| " | " | " | " | CH₂OH in 5 | " | " | " | " |
| " | " | " | " | OH in 6 | " | " | " | " |
| " | " | " | " | OH in 5 | " | " | " | " |
| " | " | " | " | CO₂CH₃ in 6 | " | " | " | " |
| " | " | " | " | CO₂CH₃ in 5 | " | " | " | " |
| " | " | " | " | COOH in 6 | " | " | " | 2-(SO₂—NH—CO—NH—C₆H₅)phenyl |
| " | " | " | " | COOH in 5 | " | " | " | " |
| " | " | " | " | CH₂OH in 6 | " | " | " | " |
| " | " | " | " | CH₂OH in 5 | " | " | " | " |
| " | " | " | " | OH in 6 | " | " | " | " |
| " | " | " | " | OH in 5 | " | " | " | " |
| " | " | " | " | CO₂CH₃ in 6 | " | " | " | " |
| " | " | " | " | CO₂CH₃ in 5 | " | " | " | " |
| nBu | —CH= | S | —CH= | H | H | | — | 2-COOH-phenyl |
| " | " | " | " | OH in 4 | " | " | " | " |
| " | " | " | " | OH in 4 | OH 6 | " | " | " |

-continued

| $R_b$ | $Z_1$ | $Z_2$ | $Z_3$ | $R_{1b}$ | $R_{2b}$ | $Y_{1b}$ | $B_b$ | $Y_{2b}$ |
|---|---|---|---|---|---|---|---|---|
| " | " | " | " | COOH in 6 | " | " | " | " |
| " | " | " | " | $CO_2CH_3$ in 6 | " | " | " | " |
| " | " | " | " | $CH_2OH$ in 6 | " | " | " | " |
| " | " | " | " | $CH_2OCH_3$ in 6 | " | " | " | " |
| " | " | " | " | $CH_2OH$ in 4 | " | " | " | " |
| " | " | " | " | H | H | " | " | 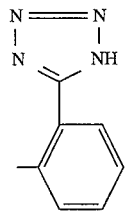 |
| " | " | " | " | COOH in 4 | " | " | " | " |
| " | " | " | " | COOH in 6 | " | " | " | " |
| " | " | " | " | OH in 4 | " | " | " | " |
| " | " | " | " | $CO_2CH_3$ in 6 | " | " | " | " |
| " | " | " | " | OH in 4 | OH in 6 | " | " | " |
| " | " | " | " | $CH_2OH$ in 6 | " | " | " | " |
| " | " | " | " | $CH_2OCH_3$ in 6 | " | " | " | " |
| " | " | " | " | $CH_2OH$ in 4 | " | " | " | " |
| nBu | —CH= | S | —CH= | H | H | " | " | COOH |
| " | " | " | " | OH in 4 | " | " | " | " |
| " | " | " | " | OH in 4 | OH in 6 | " | " | " |
| " | " | " | " | COOH in 6 | H | " | " | " |
| " | " | " | " | $CO_2CH_3$ in 6 | " | " | " | " |
| nBu | —CH= | S | —CH= | $CH_2OH$ in 6 | H | — | COOH |
| " | " | " | " | $CH_2OCH_3$ in 6 | " | " | " | " |
| " | " | " | " | $CH_2OH$ in 4 | " | " | " | " |
| " | " | " | " | COOH in 6 | " | " | " | 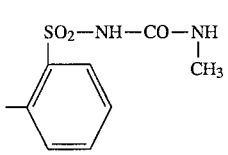 |
| " | " | " | " | COOH in 4 | " | " | " | " |
| " | " | " | " | $CH_2OH$ in 6 | " | " | " | " |
| " | " | " | " | $CH_2OH$ in 4 | " | " | " | " |
| " | " | " | " | OH in 6 | " | " | " | " |
| " | " | " | " | OH in 4 | " | " | " | " |
| " | " | " | " | $CO_2CH_3$ in 6 | " | " | " | " |
| " | " | " | " | $CO_2CH_3$ in 4 | " | " | " | " |
| " | " | " | " | COOH in 6 | " | " | " | 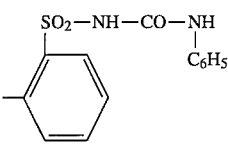 |

-continued

| $R_b$ | $Z_1$ | $Z_2$ | $Z_3$ | $R_{1b}$ | $R_{2b}$ | $Y_{1b}$ | $B_b$ | $Y_{2b}$ |
|---|---|---|---|---|---|---|---|---|
| " | " | " | " | COOH in 4 | " | " | " | " |
| " | " | " | " | CH₂OH in 6 | " | " | " | " |
| " | " | " | " | CH₂OH in 4 | " | " | " | " |
| " | " | " | " | OH in 6 | " | " | " | " |
| " | " | " | " | OH in 4 | " | " | " | " |
| nBu | —CH= | S | —CH= | CO₂CH₃ in 6 | H | | — | |
| " | " | " | " | CO₂CH₃ in 4 | " | " | " | " |
| nBu | —CH= | —CH= | S | H | H | *p-phenylene* | — | *2-(1H-tetrazol-5-yl)phenyl* |
| " | " | " | " | COOH in 4 | " | " | " | " |
| " | " | " | " | COOH in 5 | " | " | " | " |
| " | " | " | " | CO₂CH₃ in 5 | " | " | " | " |
| " | " | " | " | CH₂OH in 5 | " | " | " | " |
| " | " | " | " | CH₂OCH₃ in 5 | " | " | " | " |
| " | " | " | " | CH₂OH in 4 | " | " | " | " |
| " | " | " | " | CO₂CH₃ in 4 | H | " | " | " |
| " | " | " | " | OH in 4 | " | " | " | " |
| " | " | " | " | OH in 5 | " | " | " | " |
| " | " | " | " | H | H | " | " | COOH |
| " | " | " | " | OH in 4 | " | " | " | " |
| " | " | " | " | OH in 5 | " | " | " | " |
| " | " | " | " | COOH in 5 | " | " | " | " |
| " | " | " | " | CO₂CH₃ in 5 | " | " | " | " |
| " | " | " | " | CH₂OH in 5 | " | " | " | " |
| nBu | —CH= | S | —CH= | CH₂OCH₃ in 5 | H | | — | COOH |
| " | " | " | " | CH₂OH in 4 | " | " | " | " |
| " | " | " | " | COOH in 4 | " | " | " | " |
| " | " | " | " | CO₂CH₃ in 4 | " | " | " | " |
| " | " | " | " | H | H | " | " | *2-carboxyphenyl* |
| " | " | " | " | OH in 4 | " | " | " | " |
| " | " | " | " | COOH in 5 | " | " | " | " |
| " | " | " | " | CO₂CH₃ in 5 | " | " | " | " |
| " | " | " | " | CH₂OH in 5 | " | " | " | " |
| " | " | " | " | CH₂OCH₃ in 5 | " | " | " | " |
| " | " | " | " | CH₂OH in 4 | " | " | " | " |
| " | " | " | " | COOH | " | " | " | " |

-continued

| $R_b$ | $Z_1$ | $Z_2$ | $Z_3$ | $R_{1b}$ | $R_{2b}$ | $Y_{1b}$ | $B_b$ | $Y_{2b}$ |
|---|---|---|---|---|---|---|---|---|
| " | " | " | " | $CO_2CH_3$ in 4 | " | " | " | " |
| " | " | " | " | OH in 5 | " | " | " | " |
| " | " | " | " | $CH_2OH$ in 5 | OH | " | " | " |
| " | " | " | " | COOH in 5 | " | " | " | " |
| nBu | —CH= | S | —CH= | $CO_2CH_3$ in 5 | OH |  | — | 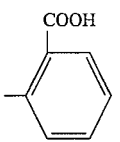 COOH |
| " | " | " | " | COOH in 4 | " | " | " | 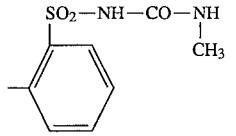 $SO_2$—NH—CO—NH<br>\|<br>$CH_3$ |
| " | " | " | " | COOH in 5 | " | " | " | " |
| " | " | " | " | $CH_2OH$ in 4 | " | " | " | " |
| " | " | " | " | $CH_2OH$ in 5 | " | " | " | " |
| " | " | " | " | OH in 4 | " | " | " | " |
| " | " | " | " | OH in 5 | " | " | " | " |
| " | " | " | " | $CO_2CH_3$ in 4 | " | " | " | " |
| " | " | " | " | $CO_2CH_3$ in 5 | " | " | " | " |
| " | " | " | " | COOH in 4 | " | " | " | 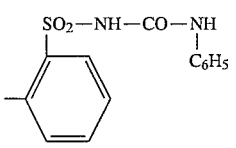 $SO_2$—NH—CO—NH<br>\|<br>$C_6H_5$ |
| " | " | " | " | COOH in 5 | " | " | " | " |
| " | " | " | " | $CH_2OH$ in 4 | " | " | " | " |
| " | " | " | " | $CH_2OH$ in 5 | " | " | " | " |
| " | " | " | " | OH in 4 | " | " | " | " |
| " | " | " | " | OH in 5 | " | " | " | " |
| " | " | " | " | $CO_2CH_3$ in 4 | " | " | " | " |
| " | " | " | " | $CO_2CH_3$ in 5 | " | " | " | " |

Furthermore, among the compounds of formula I corresponding to formula $I_c$ as defined above, the following compounds constitute the preferred compounds of the invention of formula

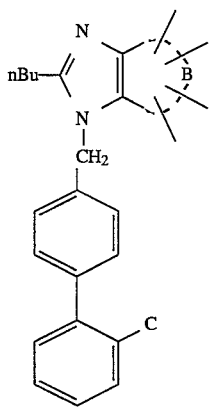

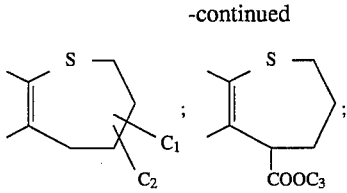

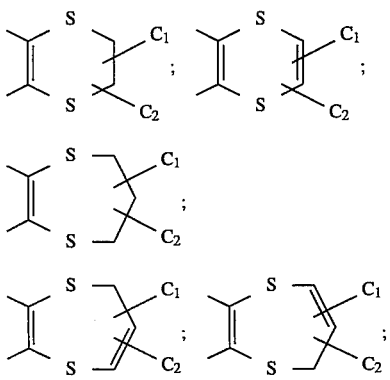

b) 2 sulfur atoms and 4 to 5 links such as:

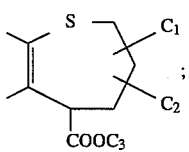

wherein C is formyl, cyano, free, salified or esterified carboxy, optionally substituted or salified tetrazolyl and $SO_2$—$X_b$—$R_{14b}$ as defined above and especially
—$SO_2$—NH—CO—NH—$CH_2$—CH=$CH_2$
and the rest of of the B ring contains 4 or 5 links, individually selected from the group consisting of S, —C=O—, optionally substituted =CH—, N optionally substituted with a formyl or free, salified or esterified carboxy and =$CH_2$ optionally substituted by 1 or 2 optional substituents of selected from the group consisting of alkyl of 1 to 4 carbon atoms such as methyl, ethyl, propyl, isopropyl, n-butyl and optionally substituted such as hydroxy methyl, free, salified or esterified carboxy, aryl such as phenyl, pyridyl, pyrimidyl aralkyl such as benzyl, pyridylmethyl, amino and carbamoyl optionally substituted by one or two alkyl or by acyl.

Thus is a non-exhaustive manner one can cite the following which contains:

a) 1 sulfur atom and 4 to 5 links such as

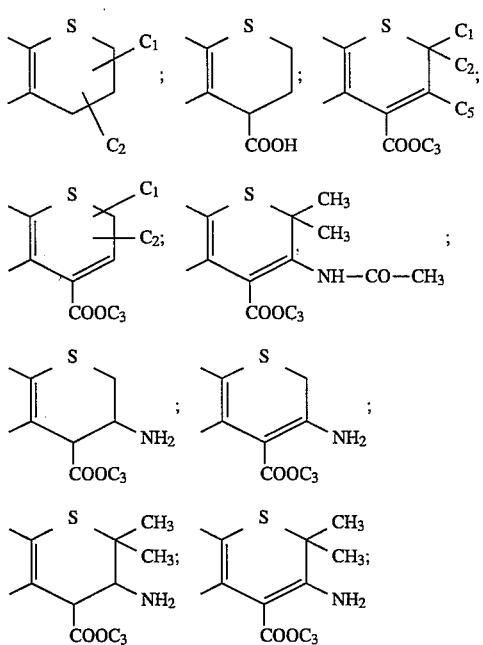

c) one sulfur atom and one nitrogen atom and 4 to 5 links such as:

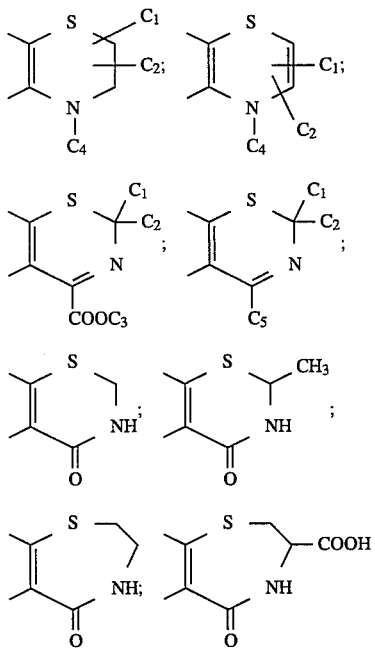

d) 2 sulfur atoms and 1 nitrogen atom and 4 links such as:

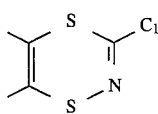

In the formulae aboe, $C_1$, $C_2$ and $C_5$ are chosen among the group of —$CH_2OH$, COOH, alkyl of 1 to 4 carbon atoms and aryl notably phenyl, $C_3$ is selected from hydrogen, 1 to 4 carbon atoms alkyl and aryl notably phenyl, $C_4$ is selected from hydrogen and formyl and $COOC_3$ in which $C_3$ has the previous definitions.

In the tables indicated above, the products can contain for $Y_2$ or $Y_{2a}$ phenyl substituted by another group of the formula —$(CH_2)_m$—$SO_2$—X—$R_{14}$ of which examples are given above in a non-exhaustive list and thus also constitute products which can be obtained within the scope of the present invention.

In the following examples, there are described several preferred embodiments to illustrate the invention. However, it is to be understood that the invention is not intended to be limited to the specific embodiments.

EXAMPLE 1

Methyl 2-butyl-1-((4-cyanophenyl)-methyl)-1H-benzimidazol-6-carboxylate and its methyl 5-carboxylate homologue STEP A: Methyl 2-butyl-1H-benzimidazole-5-carboxylate 5.47 g of ethyl pentanimidoate hydrochloride (J.A.C.S., Vol. 64, p. 1827 (1942)) were added to a solution of 5 g of methyl 3,4-diaminobenzoate in 60 ml of tetrahydrofuran, and the mixture was stirred for 3 hours and 30 minutes at 90° C. The tetrahydrofuran was evaporated off and 50 ml of a saturated solution of sodium bicarbonate were added. The mixture was extracted with methylene chloride and the extracts were washed with water, dried and evaporated to dryness under reduced pressure to obtain 9 g of product which was crystallized from isopropyl ether to obtain 6.65 g of the desired product melting at 114° C.

Analysis: $C_{13}H_{16}N_2O_2$; molecular weight=232.27 Calculated: % C 67.22% H 6.94% N 12.06 Found: 67.3 6.8 11.3

IR Spectrum: $CHCl_3$

| | |
|---|---|
| =C—NH | 3456 cm$^{-1}$ |
| >=O | 1712 cm$^{-1}$ |
| $CH_3$ of $COOCH_3$ | 1438 cm$^{-1}$ |
| Aromatics + conjugated system | 1588–1576–1546 cm$^{-1}$ |

STEP B: Methyl 2-butyl-1-((4-cyanophenyl)-methyl)-1H-benzimidazole-6-carboxylate (product A) and its methyl 5-carboxylate isomer (product B)

960 mg of sodium hydride in a 50% dispersion in oil were added to a solution of 4.64 g of the product of Step A in 46 ml of dimethylformamide. The mixture was stirred for 90 minutes at ambient temperature and 4.4 g of 4-bromomethyl benzonitrile were added. After stirring for 30 minutes, 100 ml of water were added slowly, followed by stirring for 30 minutes, separating, washing with water and drying at 100° C. under reduced pressure to obtain 7.4 g of crude product melting at 140° C.

Isolation of product A:

7.4 g of the product were dissolved in 400 ml of ethyl acetate at reflux and the solution was filtered while hot and concentrated to a total volume of 100 ml. The mixture was stirred for one hour at ambient temperature and after separating, 3.4 g of the desired product melting at 200° C. to 205° C. were obtained.

Isolation of product B:

The mother liquors of product A were evaporated to dryness and the residue were crystallized from isopropyl ether to obtain 3.35 g of the expected product melting at 120° C.

Analysis: $C_{21}H_{21}N_3O_2$; molecular weight=347.4 Calculated: % C 72.06 % H 6.09 % N 12.10 Found Isomer A 72.7 5.9 12.1 Found Isomer B 72.4 5.8 12.0

NMR Spectrum: ($CDCl_3$, 400 MHz)

| | Isomer A | Isomer B |
|---|---|---|
| $\underline{CH_3}$—$(CH_2)_3$— | 13.7 | 13.7 |
| $CH_3$—$\underline{CH_2}$—$(CH_2)_2$— | 22.5 | 22.5 |
| $CH_3$—$CH_2$—$\underline{CH_2}$— | 27.4 | 27.3 |
| $CH_3$—$(CH_2)_2$—$\underline{CH_2}$— | 29.4 | 29.4 |
| \N—$\underline{CH_2}$—$C_6H_4$ | 46.5 | 46.6 |
| C=N | 188.1 | 118.1 |
| \N—C/ | 134.8 | 138.2 |
| =N—C\ | 146.2 | 142.3 |
| $COOCH_3$ | 52.1 | 52.0 |
| Aromatics | 111.1 to140.8 (10H) | 108.7 to 140.8((10H) |

EXAMPLE 2

2-butyl-1-((4-carboxyphenyl)-methyl)-1H-benzimidazol-6-carboxylic acid

A solution of 500 mg of product A of Example 1 in 2.5 ml of a solution of equal parts of sulfuric acid, acetic acid and water was stirred for 19 hours at reflux and after cooling, 30 g of ice were added. Alkalization was done with sodium hydroxide and then the pH was adjusted to 6 with acetic acid, followed by stirring for 15 minutes at ambient temperature, separating, washing with water and drying at 90° C. under reduced pressure to obtain 480 mg of product melting at approximately 290° C.

Purification:

556 mg of the product were dissolved in 30 ml of methanol at reflux and the solution was concentrated to 10 ml. 2 ml of water were added and then after crystallization was started, 20 ml of water were added. After 3 hours, the crystals were separated and washed 3 times with 5 ml of a methanol-water mixture (1-1) to obtain 490 mg of product melting at 290° C. The 490 mg of product were dissolved in 40 ml of isopropanol at reflux, and the solution was concentrated to 15 ml. It was maintained at ambient temperature for 16 hours and separated to obtain 430 mg of the desired product melting at 290° C.

Analysis: $C_{20}H_{20}N_2O_4$; molecular weight=352.38
Calculated: % C 68.17 % H 5.72 % N 7.95 Found: 68.4 5.8 8.0

IR Spectrum: Nujol

| C=O | 1725 cm$^{-1}$ |
| --- | --- |

NMR Spectrum: DMSO, 400 MHz

| CH$_3$ | 0.86(t) |
| --- | --- |
| 2 Central CH$_2$'s | 1.35(m) and 1.71(m) |
| the other CH$_2$ of the chain | 2.87(m) |
| N—CH$_2$— | 5.70(s) |
| Aromatics | 7.16 (d) and 7.91(d) 4H |
| the other aromatics | 7.67(d), 7.82(d), 8.05(s) |
| mobile H of the diacid | 12.88(m) 2H. |

EXAMPLE 3

2-butyl-1-((4-carboxyphenyl)-methyl-1H-benzimidazol-5-carboxylicacid

Using the procedure of Example 2, 500 mg of product B of Example 1 were reacted to obtain 390 mg of crude product melting at 200° C. The crude product was dissolved in 10 ml of ethanol at 60° C. and 10 ml of water were added. The mixture stood for 2 hours at ambient temperature and after separating, 260 mg of product were obtained which was dissolved in 150 ml of ethyl acetate at reflux. The solution was concentrated to a total volume of 30 ml, stood for 16 hours at ambient temperature and separated to obtain 220 mg of the expected product melting at approximately 225° C.

Analysis: $C_{20}H_{20}N_2O_4$; molecular weight=352.38
Calculated: % C 68.17 % H 5.72 % N 7.95 Found: 68.2 5.7 7.9

IR Spectrum: Nujol

| C=O | 1717 and 1685 cm$^{-1}$ |
| --- | --- |

EXAMPLE 4

4-((2-butyl-1H-benzimidazol-1-yl)-methyl)-benzonitrile

Using the procedure of Step B of Example 1, 3.5 g of 2-butyl-1H-benzimidazol [POOL et al., Am. Soc., Vol. 59, p. 178 (1937)] and 4.3 g of 4-bromomethyl benzonitrile were reacted to obtain 6.8 g of the desired product melting at 130° C. which was dissolved in methylene chloride, treated with activated charcoal, filtered and evaporated to dryness to obtain 6 g of product melting at 130° C. which was crystallized from isopropyl ether to obtain 4.7 g of the expected product melting at 148° C. The analytical sample was obtained by two successive crystallizations of 1.2 g of the product from isopropyl ether to obtain 700 mg of purified product melting at 150° C.

Analysis: $C_{19}H_{19}N_3$; molecular weight=289.381
Calculated: % C 78.86 % H 6.62 % N 14.52 Found: 79.0 6.6 14.6

EXAMPLE 5

4-((2-butyl-1H-benzimidazol-1-yl)-methyl)benzoic acid

Using the procedure of Example 2, 1 g of the product of Example 4 was reacted to obtain 1 g of the desired product which was crystallized from 10 ml of ethyl acetate to obtain 900 mg of the expected product melting at 235° C. The analytical sample was obtained by two successive crystallizations from isopropanol to obtain 500 mg of pure product melting at 235° C.

Analysis: $C_{19}H_{20}N_2O_2$; molecular weight=308.88
Calculated: % C 73.99 % H 6.54 % N 9.08 Found: 74.0 6.6 9.3

IR Spectrum: (Nujol)

| Absorption OH/NH complex region | |
| --- | --- |
| $\rangle$=O | 1690 cm$^{-1}$ |
| Aromatics | 1610 cm$^{-1}$ |
| + | 1579 cm$^{-1}$ |
| Heteroatom | 1508 cm$^{-1}$ |

EXAMPLE 6

4-((2-butyl-1H-benzimidazol-1-yl)-methyl)-N-(1H-indol-4-yl)benzamide 192 mg of 1-ethyl-3-(3-dimethylaminopropyl)-carbodiimide hydrochloride were added to a suspension of 180 mg of the product of Example 5 in 4 ml of methylene chloride and after stirring for 10 minutes at ambient temperature, 53 mg of 4-amino indole were added. After stirring for 18 hours and extraction with 2 lots of 25 ml of methylene chloride, the extracts were washed with water, dried and evaporated to dryness under reduced pressure to obtain 230 g of residue which was chromatographed on silica (eluant: methylene chloride-methanol (95-5)) to obtain 115 mg of the desired product melting at 196° C. After crystallization from ethyl acetate, 87 mg of the desired product melting at 196° C. were obtained.

Analysis: $C_{27}H_{26}N_4O$; molecular weight=422.51
Calculated: % C 76.76 % H 6.20 % N 13.26 Found: 77.2 6.2 13.3

IR Spectrum: (Nujol)

| C=O | 1640 cm$^{-1}$ |
| --- | --- |
| Aromatic | 1611 cm$^{-1}$ |
| + | |
| heteroatom | 1575 cm$^{-1}$ |
| + | |
| amide II | 1528 cm$^{-1}$ |
| | 1492 cm$^{-1}$ |

EXAMPLE 7

Methyl 2-butyl-1-((4-cyanophenyl)-methyl)-1H-benzimidazol-4-carboxylate

STEP A: Methyl 2-butyl-1H-benzimidazole-4-carboxylate

Using the procedure of Step A of Example 1, 2.5 g of methyl 2,3-diaminobenzoate [J. Chem. Soc., Vol. 117 (1920) p 775 and CAN. J. Chem., Vol.55 (1977), p. 1653 to 1657] and 2.73 g of ethyl pentanimidoate hydrochloride [J.A.C.S., Vol. 64, p. 1827 (1942)] were reacted to obtain 3.05 g of the desired product which after crystallization from essence G melted at approximately 85° C. The analytical sample was obtained by two successive crystallizations of 280 mg of product from isopropyl ether to obtain 100 mg of the product melting at 97° C.

Analysis: $C_{13}H_{16}N_2O_2$; molecular weight=232.29 Calculated: % C 67.22 % H 6.94 % N 12.06 Found: 67.1 7.0 12.0

IR Spectrum: $CHCl_3$)

| | |
|---|---|
| =C—NH | 3448 cm$^{-1}$ |
| >=O complex | 1728 cm$^{-1}$ |
| | 1699 cm$^{-1}$ |
| conjugated system | 1626 cm$^{-1}$ |
| + | 1606 cm$^{-1}$ |
| Aromatic | 1522 cm$^{-1}$ |
| | 1495 cm$^{-1}$ |

STEP B: Methyl 2-butyl-1-((4-cyanophenyl)-methyl)-1H-benzimidazol-4-carboxylate

Using the procedure of Step B of Example 1, 1.86 g of the product of Step A and 1.88 g of 4-bromomethyl benzonitrile were reacted to obtain 3.5 g of product which was chromatographed on silica (eluant: ethyl acetate-cyclohexane (6-4)) to obtain 2.05 g of the desired product which after crystallization from ethyl ether melted at 113° C.

NMR Spectrum: ($CDCl_3$, 250 MHZ)

| | |
|---|---|
| $\underline{CH_3}$—$(CH_2)_2$ | 0.92 ppm (t) |
| central $CH_2$'s | 1.43–1.82 ppm (m) |
| >—$\underline{CH_2}$—$CH_2$ | 2.92 ppm (t) |
| $CO_2CH_3$ | 4.04 ppm (s) |
| N—$\underline{CH_2}$—$C_6H_5$ | 5.44 ppm |
| benzonitrile | 7.09–7.61 ppm (d) |
| $H_5$ | 7.95 ppm (dd) |
| $H_6$, $H_7$ | approximately 7.27 ppm (m). |

EXAMPLE 8

2-butyl-1-((4-carboxyphenyl)-methyl)-1H-benzimidazol-4-carboxylic acid

Using the procedure of Example 2, 1 g of the product of Example 7 was reacted to obtain 1 g of the desired product melting at 250° C. The analytical sample was obtained after 2 successive crystallizations from a methylene chloride-methanol mixture to obtain 345 mg of the product melting at 250° C.

Analysis: $C_{20}H_{20}N_2O_4$; molecular weight=352.39 Calculated: % C 68.17 % H 5.72 % N 7.95 Found: 68.3 5.8 8.1

NMR Spectrum: (DMSO, 250 MHZ).

| | |
|---|---|
| $\underline{CH_3}$—$(CH_2)$ | 0.87 ppm (t) |
| $\underline{CH_3}$—$(CH_2)_2$— | 1.37–1.71 ppm (m) |
| =C—$\underline{CH_2}$ | 2.93 ppm (t) |
| N—$\underline{CH_2}$—$C_6H_5$ | 5.71 ppm (s) |
| —$C_6H_4$—CO | 7.21–7.91 ppm (dl) |
| $H_6$ | 7.36 ppm (t) |
| $H_5$, $H_7$ | 7.80 ppm (dd) |

EXAMPLE 9

4-((2-butyl-1H-naphth(2,3-d)imidazol-1-yl)-methyl)-benzonitrile

STEP A: 2-butyl-1H-naphth(2,3-d)imidazole

Using the procedure of Step A of Example 1, 2.7 g of 2,3-diaminonaphthalene and 3.4 g of ethyl pentanimidoate hydrochloride [J.A.C.S., Vol. 64, p. 1827 (1942)] in dichloroethane as solvent were reacted to obtain 4.5 g of crude product which was dissolved in 100 ml of ethyl acetate at reflux. The solution was concentrated to a total volume of 30 ml and stood for 16 hours and separated to obtain 2.37 of the desired product melting at 188° C. An analytical sample was obtained by successive crystallization of 500 mg of the product from ethyl acetate, then from isopropanol to obtain 280 mg of the expected product melting at 190° C.

Analysis: $C_{15}H_{16}N_2$; molecular weight=224.29 Calculated: % C 80.32 % H 7.19 % N 12.49 Found: 80.1 7.2 12.4

NMR Spectrum (DMSO, 250 MHz)

| | |
|---|---|
| $\underline{CH_3}$—$(CH_2)$ | 0.94 ppm (t) |
| $CH_3$—$(\underline{CH_2})$—$(\underline{CH_2})$— | 1.41–1.83(m) |
| >—C—$\underline{CH_2}$— | 2.91(t) |
| Aromatics | 7.35(m)2H–7.97(m)4H |
| mobile 1H | 12.29(sl) |

STEP B: 4-((2-butyl-1H-naphth(2,3-d)imidazol-1-yl)-methyl)-benzonitrile

Using the procedure of Step B of Example 1, 449 mg of the product of Step A and 392 mg of 4-bromomethyl benzonitrile were reacted to obtain 460 mg of the desired product melting at 138° C. after crystallization from ethyl ether.

EXAMPLE 10

4-((2-butyl-1H-naphth(2,3-d)imidazol-1-yl)-methyl)benzoic acid

A suspension of 420 mg of the product of Example 9 in 4 ml of ethanol and 7.5 ml of 2N of sodium hydroxide was refluxed for 21 hours and after cooling the suspension, 5 ml of ice were added. The mixture was neutralized to pH 7 with 7.5 ml of 2N hydrochloric acid and 30 ml of methanol were added, followed by heating to reflux and concentrating to 20 ml. After separating, 420 mg of the expected product were obtained. The 420 mg of above product were crystallized successively from isopropanol, then from ethyl acetate to obtain 260 mg of pure product melting at 220° C.

Analysis: $C_{23}H_{22}N_2O_2$; molecular weight=358.44 Calculated: % C 77.07 % H 6.19 % N 7.82 Found: 76.8 6.0 7.6

NMR Spectrum: (DMSO, 400 MHZ)

| | |
|---|---|
| $\underline{CH_3}$—$CH_2$ | 0.87 ppm (t) |
| $CH_3$—$\underline{CH_2}$—$\underline{CH_2}$ | 1.38 and 1.76 ppm (m) |
| $\underline{CH_2}$—C< | 2.89 ppm (t) |
| N—$\underline{CH_2}$—$C_6H_5$ | 5.68 ppm (s) |
| C—$C_6H_4$—C< | 7.22 and 7.89 ppm (d) |
| Aromatics | 7.36(m)2H–7.89(m)2H–7.99(m)1H–8.14(s)1H |

| | |
|---|---|
| mobile H | 12.96(s) |

EXAMPLE 11

4-((2-butyl-3H-imidazo(4,5-d)pyrimidin-3-yl)-methyl)benzonitrile (product A) and 4-((2-butyl-3H-imidazo(5,6-d)pyrimidine-3-yl)-methyl)benzonitrile (product B)

STEP A: 2-butyl-3H-imidazo-(4,5-d)pyrimidine

Using the procedure of Example 1, 5 g of 4,5-diaminopyrimidine and 10 g of ethyl pentanimidoate hydrochloride [J.A.C.S., Vol. 64, p 1827 (1942)] using dimethylformamide as solvent were reacted to obtain 2.1 g of the desired product which after crystallization from ethyl acetate melted at 166° C. The product was crystallized from ethyl acetate to obtain 1.8 g of the expected product melting at 168° C. 200 mg of an analytical sample was obtained by an additional crystallization of 300 mg of the product from ethyl acetate melting at 168° C.

Analysis: $C_9H_{12}N_4$; · molecular weight=176.22 Calculated: % C 61.34 % H 6.86 % N 31.8 Found: 61.3 6.9 31.9

NMR Spectrum: (CDCl$_3$, 250 MHz)

| | |
|---|---|
| $CH_3-$ | 1.01 ppm (t) |
| $CH_3-\underline{CH_2}-\underline{CH_2}$ | 1.53 and 1.99(m) |
| $\underline{CH_2}-C\langle$ | 3.12(t) |
| Aromatics | 8.99 and 9.13(s) |
| mobile H | 13.45(sl) |

STEP B: 4-((2-butyl-3H-imidazo(4,5-d)pyrimidin-3-yl)-methyl)benzonitrile (Product A) and 4-((2-butyl-3H-imidazo-(5,6-d)pyrimidin-3-yl)-methyl)-benzonitrile (Product B)

using the procedure of Step B of Example 1, 352 mg of the compound of Step A and 431 mg of 4-bromoethyl benzonitrile were reacted to obtain 630 mg of crude product which was chromatographed on silica (eluant: methylene chloride-methanol (9-1)) to obtain 130 mg of product A, which after crystallization from ethyl ether melted at 112° C. and 35 mg of product B which melted at 85° C. after crystallization from a methyl-ethyl-ketone-ether mixture.

Product A:

Analysis: $C_{17}H_{17}N_5$; molecular weight=291.35 Calculated: % C 70.08 % H 5.88 % N 24.04 Found: 70.0 5.8 23.9

NMR Spectrum: (CDCl$_3$, 300 MHz ppm)

| | |
|---|---|
| $CH_3-$ | 0.93(t) |
| $CH_3-\underline{CH_2}-\underline{CH_2}$ | 1.42 and 1.82(m) |
| $\underline{CH_2}-\langle$ | 2.80(m) |
| $N-\underline{CH_2}-$ | 5.52(s) |
| Aromatics | 7.27–7.65(d, 1) |
| Heterocycle | 8.94 and 9.08(s) |

Product B:

NMR Spectrum: (CDCl$_3$, 300 MHz ppm)

| | |
|---|---|
| $CH_3-$ | 0.94(t) |
| $CH_3-\underline{CH_2}-\underline{CH_2}$ | 1.44 and 1.88(m) |
| $\rangle C-\underline{CH_2}-$ | 2.90(m) |
| $-N-\underline{CH_2}-$ | 5.49(s) |
| Aromatics | 7.18–7.68(d, 1) |
| Heterocycle | 8.60 and 9.09(s). |

EXAMPLE 12

4-((2-butyl-3H-imidazo(4,5-d)pyrimidin-3-yl)-methyl benzoic acid 400 mg of the product A of Example 11 and 8 ml of ethanol with 10% water and 1 ml of sodium hydroxide were stirred for 2 hours at reflux and after 20 ml of water were added, the mixture was neutralized to pH 5–6 with acetic acid and extracted with methylene chloride. The extracts were washed, dried and evaporated to dryness under reduced pressure to obtain 280 mg of the expected product which after crystallization from an ethyl acetate-ether mixture melted at 165° C. The product was crystallized twice in succession from methyl ethyl ketone to obtain 185 mg of the desired compound melting at 173° C.

Analysis: $C_{17}H_{18}N_4O_2$; molecular weight=310.35 Calculated: % C 65.79 % H 5.85 % N 18.05 Found: 65.8 5.9 18.0

NMR Spectrum: (DMSO, 250 MHz ppm):

| | |
|---|---|
| $CH_3-$ | 0.84(t) |
| $CH_3-\underline{CH_2}-\underline{CH_2}$ | 1.34 and 1.68(m) |
| $\rangle C-\underline{CH_2}-$ | 2.86(t) |
| $N-\underline{CH_2}-$ | 5.62(s) |
| Heterocycle | 8.90 and 9.09(sl) |
| Aromatics | 7.28 and 7.92(d, 1) |
| Mobile H | 12.88(m). |

EXAMPLE 13

4-((2-butyl-3H-imidazo(5,6-d)pyrimidin-3-yl)-methyl)benzoic acid

Using the procedure of Example 12, product B of Example 11, was reacted to obtain the expected compound melting at 180° C.

EXAMPLE 14

4-((2-butyl-5,6-dimethyl-1H-benzimidazol-1-yl)-methyl)benzonitrile

STEP A: 2-butyl-5,6-dimethyl-1H-benzimidazole

Using the procedure of Step A of Example 1, 2.04 g of 4,5-dimethyl-1,2-phenylene diamine and 3.73 g of ethyl pentanimidoate hydrochloride [J.A.C.S., Vol. 64, p. 1827 (1942)] were reacted to obtain 3.48 g of crude product which was chromatographed on silica (eluant: methylene chloride-methanol (9-1)) to obtain 2.27 g of the expected compound melting at 110° C. An analytical sample was prepared by crystallization of 120 mg of the product from isopropyl ether to obtain 88 mg of product melting at 110° C.

Analysis: $C_{17}H_{18}N_4O_2$; molecular weight=310.35
Calculated: % C 65.79 % H 5.85 % N 18.05 Found: 65.8 5.9 18.0
IR Spectrum: ($CHCl_3$)

| =C—NH | 3470 $cm^{-1}$ |
|---|---|
| C=N | 1634 $cm^{-1}$ |
| Aromatic | 1585 $cm^{-1}$ |
|  | 1538 $cm^{-1}$ |

STEP B: 4-((2-butyl-5,6-dimethyl-1H-benzimidazol-1-yl)-methylbenzonitrile

Using the procedure of Step B of Example 1, 2.02 g of the product of Step A and 2.21 g of 4-bromomethyl benzonitrile were reacted to obtain 2.88 g of the desired product which after crystallization from ether melted at 159° C. The analytical sample was prepared by crystallization of 476 mg of product from isopropanol, then from ethyl acetate to obtain 132 mg of the expected product melting at 160° C.
Analysis: $C_{21}H_{23}N_3$; molecular weight=317.43
Calculated: % C 79.46 % H 7.30 % N 13.24 Found: 79.7 7.5 13.1
NMR Spectrum: ($CDCl_3$, 250 MHz ppm).

| $CH_3$— | 0.90(t) |
|---|---|
| $CH_3\underline{CH}_2$—$\underline{CH}_2$ | 1.40–1.78(m) |
| $\rangle C-\underline{CH}_2$— | 2.75(m) |
| 2 $\underline{CH}_3$—$C_6H_3$ | 2.31–2.36(s) |
| N—$\underline{CH}_2$—$C_6H_4$ | 5.34(s) |
| 2H | 6.87–7.63(s) |

EXAMPLE 15

4-((2-butyl-5,6-dimethyl-1H-benzimidazol-1-yl)-methyl)benzoic acid

Using the procedure of Example 12, 395.7 mg of the product of Example 14 were reacted to obtain 367 mg of the expected product melting at 220° C. The analytical sample was obtained by crystallizing the product twice from isopropanol to obtain 198 mg of pure product melting at 254° C.
Analysis: $C_{21}H_{24}N_2O_2$; molecular weight 336.44
Calculated: % C 74.97 % H 7.19 % N 8.33 Found: 74.8 7.3 8.3
NMR Spectrum: (DMSO, 259 MHz ppm)

| $CH_3$— | 0.89(t) |
|---|---|
| $CH_3$—$\underline{CH}_2$—$\underline{CH}_2$— | 1.33 and 1.66(m) |
| $\rangle C-\underline{CH}_2$— | 2.75(t) |
| the $CH_3$—C$\langle$'s | 2.26 and 2.29(s) |
| N—$\underline{CH}_2$—$C_6H_4$ | 5.51(sl) |
| Aromatics | 7.17–7.85(d) |
| Other aromatics | 7.11–7.36(s) |

EXAMPLE 16

1H-benzimidazol methyl benzonitrile

Using the procedure of Step B of Example 1, 951 mg of benzimidazole and 1.97 g of 4-bromomethyl benzonitrile in dimethylformamide were reacted to obtain 2.48 g of crude product which was chromatographed on silica (eluant: methylene chloride-methanol (95-5)) to obtain 1.34 g of the desired product melting at 94° C. after Crystallization from ether. An analytical sample was prepared by two successive crystallizations of 422 mg of the product from ether, then from isopropyl ether to obtain 167 mg of pure product melting at 94° C.
Analysis: $C_{15}H_{11}N_3$; molecular weight=233.28
Calculated: % C 77.23 % H 4.75 % N 18.02 Found: 77.5 4.6 17.9
NMR Spectrum: (DMSO, 250 MHz ppm)

| N—$\underline{CH}$=N | 8.45(s) |
|---|---|
| Aromatics | 7.21(m) 2H |
| (benzimidazole) | 7.46(m) 1H |
|  | 7.69(m) 1H |
| the other aromatics | 7.45(d) |
|  | 7.83(d) |
| N—$\underline{CH}_2$—$C_6H_4$ | 5.64 |

EXAMPLE 17

4((1H-benzimidazol-1-yl)-methyl benzoic acid

Using the procedure of Example 12, 921 mg of the compound of Example 16 were reacted to obtain 888 mg of the desired product melting at 260° C. An analytical sample was prepared by two crystallizations of the product from isopropanol, then from ethyl acetate to obtain 390 mg of pure product melting at 260° C.
Analysis: $C_{15}H_{12}N_2O_2$; molecular weight 252.28
Calculated: % C 71.42 % H 4.79 % N 11.11 Found: 71.2 4.7 11.1
NMR Spectrum: (DMSO, ppm)

| N—$\underline{CH}_2$—$C_6H_4$ | 5.62(o) |
|---|---|
| N—$\underline{CH}$— | 8.46 |
| Aromatics | 7.22(m) 2H |
|  | 7.50(m) 1H |
|  | 7.70(m) 1H |
| the other aromatics | 7.39(d) |
|  | 7.93(d) |
| Mobile H | 13.02 |

EXAMPLE 18

4-((2-butyl-1H-imidazo(4,5-c)pyridin-1-yl)-methyl benzonitrile (product A) and 4-((2-butyl-1H-imidazo(3,4-c)pyridin-1-y)-methyl)benzonitrile (product B)

STEP A: 2-butyl-1H-imidazo(4,5-c)pyridine

A mixture of 3 g of 3,4-diamino-pyridine and 8.28 g of valeric acid was heated to 70° C. for 18 hours and the reaction medium was chromatographed on silica (eluant: ethyl-acetate methanol (8-2)) to obtain 4.8 g of the expected product which was used as is for the following step.

STEP B: 4-((2-butyl-1H-imidazo(4,5-c pyridin-1-yl)-methyl)benzonitrile (product A) and 4-((2-butyl-1H-imidazo(3,4-c)pyridin-1-yl)-methyl)benzonitrile (product B)

Using the procedure of Step B of Example 1, 4.09 g of the product of Step A and 4.58 g of 4-bromomethyl benzonitrile were reacted to obtain 8.5 g of crude product which was chromatographed on silica (eluant: methylene chloride-methanol (9-1)) to obtain 290 mg of product B which after crystallization from ether melted at 130° C., and 380 mg of product A which after crystallization from ether melted 164° C.

| Analysis:<br>NMR CDCl₃ 250 MHz | Product A | Product B |
|---|---|---|
| CH₃ | 0.93(t) | 0.94(t) |
| CH₃—CH₂—CH₂ | 1.44–1.84(m) | 1.43–1.85(m) |
| >C—CH₂— | 2.82(m) | 2.85(m) |
| N—CH₂—C₆H₄ | 5.41(s) | 5.48(s) |
| Heteroatom | 9.08(s)<br>8.38(d, j=6)<br>7.10(d) masked | 7.68(d, 1, j=6)<br>8.45(d, j=6) |
| Aromatics | 7.13–7.64(d, 1, j=8) | 7.16–7.65(d, 1) |

EXAMPLE 19

4-((2-butyl-1H-imidazo(4,5-c)pyridin-1-yl)-methyl)benzoic acid

Using the procedure of Example 12, 320 mg of product A of Example 18 were reacted to obtain 320 mg of crude product melting at 210° C. The product was crystallized from isopropanol with 40% water to obtain 250 mg of the desired product melting at 246° C. which was crystallized from 10 ml of isopropanol to obtain 180 mg of the desired compound melting at 246° C.

Analysis: C₁₈H₁₉N₃O₂; molecular weight=309.37 Calculated: % C 69.88 % H 6.19 % N 13.58 Found: 70.0 6.2 13.6

NMR Spectrum: (DMSO, 250 MHz ppm)

| CH₃—<br>CH₃—CH₂—CH₂ | 0.85(t)<br>1.35–1.71(m) |
|---|---|
| —CH₂—C⟨ | 2.87(t) |
| N—CH₂—C₆H₄ | 5.64(s) |
| Heterocycle | 8.90(s) 8.29(d) 7.56(d) |
| Aromatic | 7.20 and 7.92(d) |

EXAMPLE 20

4-((2-butyl-3H-imidazo(4,5-c)pyridin-3-yl)-methyl)benzoic acid

Using the procedure of Example 12, product B of Example 18 was reacted to obtain 170 mg of product melting at 200° C. and after crystallization from isopropanol melted at 216° C.

Analysis: C₁₈H₁₉N₃O₂; molecular weight=309.37 Calculated: % C 69.88 % H 6.19 % N 13.58 Found: 70.1 6.2 13.5

NMR Spectrum: (DMSO, 250 MHz ppm)

| CH₃—<br>CH₃—CH₂—CH₂ | 0.85(t)<br>1.35–1.71(m) |
|---|---|
| —CH₂—C⟨ | 2.87(t) |
| N—CH₂—C₆H₄ | 5.69(s) |
| Heterocycle | 7.60(d) 8.30(d) 8.80(s) |
| Aromatic | 7.22(d)–7.91(d) |
| Mobile H | 12.95 |

EXAMPLE 21

4-((2-(1-butenyl)-1H-benzimidazol-1-yl)-methyl)benzonitrile

STEP A: 4-((2-(1-bromobutyl)-1H-benzimidazol-1-yl)-methyl)benzonitrile

A suspension of 1.16 g of the product of Example 4 and 36 ml of carbon tetrachloride, 712 mg of N-bromosuccinimide and a few crystals of benzyl peroxide was stirred for 2 hours at 60° C. under irradiation by a 60-watt lamp. The suspension was cooled down and extracted with methylene chloride. The extracts were washed with a saturated solution of sodium bicarbonate, then with water, dried and evaported to dryness under reduced pressure to obtain 2.1 g of residue which was chromatographed on silica (eluant: ethyl acetate-cyclohexane (1-1)) to obtain 600 mg of the desired product melting at 132° C. An analytical sample was prepared by crystallization of 100 mg of the product from 20 ml of ether to obtain 58 mg of the expected product melting at 135° C.

NMR Spectrum: (CDCl₃, 250 MHz)

| CH₃—<br>CH₂—CH₃<br>CH₂—CH₂—CH₃ | 0.91(t)<br>1.49(m)<br>2.50(m) |
|---|---|
| CH₂—CH—C—<br>\|<br>X | 4.95(d, d, j=7 and 7.5) |
| N—CH₂ | 5.56(AB)J=17.5<br>7.19(d, m) |
| Aromatics | 7.63(d, m)<br>7.85(d, d) |
| Other aromatics | 7.10 to 7.37(m) |

Analysis: C₁₉H₁₈BrN₃; molecular weight=368.27 Calculated: % Br 21.7 Found: 21.4

STEP B: 4-((2-(1-butenyl)-1H-benzimidazol-1-yl)-methylbenzonitrile 1.33 g of lithium carbonate and 1.56 g of lithium bromide were added to a solution of 1.10 g of the product of Step A in 5 ml of dimethylformamide and the mixture was stirred for 15 minutes at reflux. The dimethylformamide was evaporated off and the residue was chromatographed on silica (eluant: cyclohexane-ethyl acetate (1-1)) to obtain 480 mg of the expected product melting at 125° C. after crystallization from ether.

NMR Spectrum: (CDCl₃, 250 MHz)

| CH₃— | 1.10(t) |
|---|---|
| CH₂—CH₃ | 2.31(m) |
| N—CH₂ | 5.44(s) |
| —CH=CH—CH₂ (delta E) | 6.31(dt, J=15.5 and 1.5)<br>7.19(d,m) |
| Aromatics | 7.61(d,m)<br>7.77(d,l) |
| Other aromatics | 7.11 to 7.32(m) |

EXAMPLE 22

4-((2-(1-butenyl)-1H-benzimidazol-1-yl)-methyl)benzoic acid

Using the procedure of Example 12, 430 mg of the product of Example 21 were reacted to obtain 450 mg of the desired product melting at 210° C., then 225° C. An analytical sample was obtained by successive crystallizations from aqueous methanol, ethyl acetate and finally aqueous methanol slightly acidified by acetic acid to obtain 150 mg of the expected product melting at 240° C.

Analysis: $C_{19}H_{18}N_2O_2$; molecular weight=306.35
Calculated: % C 74.49 % H 5.92 % N 9.15 Found: 74.6 6.0 9.0

NMR Spectrum: (DMSO, 250 MHz).

| | |
|---|---|
| $CH_3$— | 1.06(t) |
| $\underline{CH_2}$—$CH_3$ | 2.28(m) |
| N—$\underline{CH_2}$ | 5.67(s) |
| $CH_3$—$\underline{CH_2}$—CH=CH— | 6.67(d, j=16Hz) delta E |
| $CH_3$—$CH_2$—$\underline{CH}$=CH— | 7.05(d,t) J=16 and 6Hz |
| H in ortho position of COO | 7.89(d) |
| other aromatics | 7.48(m)–7.60(m)–7.1 to 7.3(m) |
| mobile hydrogen | 12.95 |

EXAMPLE 23

4-((2-butyl-3H-imidazo-(4,5-b)pyridin-1-yl)-methyl benzonitrile (Product A) and 4-((2-butyl-3H-imidazo-(4,5-b)pyridin-3yl)-methyl)benzonitrile (Product B)

STEP A: 2-butyl-3H-imidazo(4,5-b)pyridine

Using the procedure of Step A of Example 1, 3.27 g of 2,3-diaminopyridine and 6.5 ml of valeric acid were reacted to obtain after chromatography on silica (eluant: ethyl acetate-methanol (8-2)), 5.7 g of product which was treated with activated charcoal in ethyl ether and crystallized from 20 ml of isopropyl ether to obtain 3.9 g of the desired product melting at 104° C. An analytical sample was obtained by crystallization of 300 mg of the product from ethyl ether to obtain 240 mg of the desired product melting at 104° C.

Analysis: $C_{10}H_{13}N_3$; molecular weight=175.235
Calculated: % C 68.54 % H 7.48 % N 23.98 Found: 68.3 7.5 23.7

STEP B: 4-((2-butyl-3H-imidazo-(4,5-b)-pyridin-1-yl)-methyl)benzonitrile (Product A) and 4-((2-butyl-3H-imidazo-(4,5-b)pyridin-3-yl)-methyl benzonitrile (Product B)

Using the procedure of Step B of Example 1, 700 mg of the product of Step A and 200 mg of sodium hydride at 50% in oil and 800 mg of 4-bromobenzonitrile were reacted to obtain after chromatography on silica (eluant: methylene chloride-methanol (9-1)) the following:

Fraction A:

510 mg crystallized from ethyl ether melting at 130° C. which was crystallized from 3 ml of ethyl acetate to obtain 280 mg of the desired product melting at 130° C.

Fraction B:

170 mg crystallized from ethyl ether melting at 103° C. After crystllization from 3 ml of ethyl ether, 155 mg of the desired product melting at 103° C. were obtained.

Analysis: fraction A $C_{18}H_{18}N_4$; molecular weight=290.37
Calculated: % C 74.46 % H 6.25 % N 19.29 Found: 74.2 6.2 19.1

Fraction B Found: 74.2 6.2 19.2

EXAMPLE 24

4-((2-butyl)-1H-imidazo-(4,5-b)pyridin-1-yl)-methyl)benzoic acid

Using the procedure of Example 12, 250 mg of the product of Example 23, fraction A and 0.7 ml of sodium hydroxide were reacted to obtain 210 mg of the expected product melting at 190° C., which after two successive crystallizations from isopropanol yielded 140 mg of the desired product melting 200° C.

Analysis: $C_{18}H_{19}N_3O_2$; molecular weight=309.37
Calculated: % C 69.88 % H 6.19 % N 13.58 Found: 69.7 6.2 13.3

IR Spectrum (Nujol)

| Absorption OH/NH | |
|---|---|
| $>C=O$ | 1699 cm$^{-1}$ |
| conjugated system + Aromatic | 1614 cm$^{-1}$ 1580 cm$^{-1}$ 1508 cm$^{-1}$ |

EXAMPLE 25

4-((2-butyl-3H-imidazo-(4,5-b)pyridin-3-yl)-methyl benzoic acid

Using the procedure of Example 12, 130 mg of fraction B of Example 23 were reacted to obtain 110 mg of the expected product melting at 180° C. after crystallization from an isopropanol-water mixture. The product was crystallized from 2 ml of ethyl ether to obtain 80 mg of the desired product melting at 180° C.

Analysis: $C_{18}H_{19}N_3O_2$; molecular weight=309.37
Calculated: % C 69.88 % H 6.19 % N 13.58 Found: 69.6 6.2 13.4

IR Spectrum: (Nujol) Absorption region OH/NH

| | |
|---|---|
| C=O | 1698 cm$^{-1}$ |
| C=C + | 1604 cm$^{-1}$ |
| C=N + | 1598 cm$^{-1}$ |
| Aromatic | 1578 cm$^{-1}$ |
| | 1502 cm$^{-1}$ |

EXAMPLE 26

Methyl 4'-((2-butyl-3H-imidazo-(4,5-b)-pyridin-3-yl)-methyl) (1,1'-biphenyl)-2-carboxylate (fraction A) and methyl 4'-((2-butyl-1H-imidazo-(4,5-b)-pyridin-3-yl)-methyl-1,1'-biphenyl)-2-carboxylate fraction B)

Using the procedure of Step B of Example 1, 876 mg of the product of Step A of Example 23 and 250 mg of sodium hydride at 50% in oil and 1.53 g of methyl 4'-bromo-(1,1'-biphenyl)-2-carboxylate were reacted to obtain after chromatography on silica (eluant: methylene chloride-methanol (9-1)), 1.2 g of fraction A melting at 135° C., and 450 mg of fraction B.

100 mg of compound A were crystallized from ethyl ether to obtain 80 mg melting at 140° C.

NMR Spectrum: (CDCl₃, 250 MHz)

| | |
|---|---|
| CH₂—CH₂—CH₂—CH₃ | 0.94(t) |
| CH₂—<u>CH₂</u>—CH₂—CH₃ | 1.46–1.89(m) |
| <u>CH₂</u>—<u>CH₂</u>—CH₂—CH₃ | 2.92(m) |
| N—<u>CH₂</u>—C₆H₄ | 5.39(s) |
| 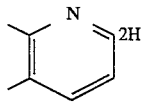 2H | 8.51(dd, J=5 and 1)<br>7.11(dd, J=8 and 5) |

Fraction B:

| | |
|---|---|
| CH₂—CH₂—CH₂—CH₃ | 0.93(t) |
| CH₂—<u>CH₂</u>—<u>CH₂</u>—CH₃ | 1.42–1.82(m) |
| <u>CH₂</u>—CH₂—CH₂—CH₃ | 2.84(m) |
| N—<u>CH₂</u>—C₆H₄ | 5.55(s) |
| 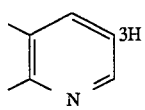 3H | 8.02(dd, J=8 and 1.5)<br>7.11(dd, J=8 and 5)<br>8.36(dd, J=5 and 1.5) |
| The aromatics | 7.18(dl) to 7.24(d, l)4H<br>7.30(d, l)1H<br>7.40(d, t)1H<br>7.51(d, t)1H<br>7.81(d, t)1H |

EXAMPLE 27

4'-((2-butyl-1H-imidazo-(4,5-b)-pyridin-1-yl)-methyl)-(1,1'-biphenyl)-2-carboxylic acid Using the procedure of Example 12, 680 mg of the product of fraction A of Example 26 and 0.7 ml of concentrated sodium hyroxide were reacted to obtain 650 mg of the desired product melting at 170° C. 900 mg of the product were dissolved in 200 ml of isopropanol at reflux, concentrated to 20 ml, and 30 ml of water were added. After separating, 810 mg of product melting at 205° C. were obtained which was crystallized from 5 ml of ethanol to obtain 640 mg of the expected product melting at 205° C.

Analysis: $C_{24}H_{23}N_3O_2$; molecular weight=385.45
Calculated: % C 74.78 % H 6.01 % N 10.9 Found: 74.45 6.0 10.7

IR Spectrum (Nujol) Absorption OH/NH complex region

| | |
|---|---|
| C=O | 1708 cm⁻¹ |
| | 1616 cm⁻¹ |
| Aromatic | 1589 cm⁻¹ |
| Heteroatom | 1574 cm⁻¹ |
| | 1500 cm⁻¹ |

EXAMPLE 28

4'-((2-butyl-3H-imidazo-4,5-b)-pyridin-3-yl)-methyl)-(1,1'-biphenyl)-2-carboxylic acid Using the procedure of Example 12, 410 mg of the product of fraction B of Example 26 and 0.4 ml of sodium hydroxide were reacted to obtain 320 mg of the expected product melting at 185° C. which was crystallized from 10 ml of an isopropanol-water mixture (1-1) to obtain 210 mg of the product melting at 190° C. The product in solution in ethyl acetate was treated with activated charcoal and filtration, concentrated to 3 ml, and separated to obtain 140 mg of the desired product melting at 190° C.

Analysis: $C_{24}H_{23}N_3O_2$; molecular weight=385.45
Calculated: % C 74.78 % H 6.01 % N 10.9 Found: 74.6 5.9 10.7

IR Spectrum (Nujol) Absorption OH/NH complex

| | |
|---|---|
| C=O | 1684 cm⁻¹ |
| Aromatic | 1600 cm⁻¹ |
| Heteroatom | 1517 cm⁻¹ |
| | 1498 cm⁻¹ |

PREPARATION OF EXAMPLES 29 and 30

STEP A: 2-nitro-3-thiophenamine 12.8 g of 85% 2-nitro-thiophene and 33.6 g of 4-amino-4H-1,2,4-triazole (1-1, 3-4) were dissolved at ambient temperature in 100 ml of anhydrous dimethyl-sulfoxide and the solution was cooled down to 5° C. A solution of 22.4 g of potassium terbutylate in 100 ml of anhydrous dimethyl-sulfoxide was added over about 15 minutes and the suspension was stirred for a further 15 minutes at ambient temperature, then poured into 0.6 liter of a saturated solution of ammonium chloride. Extraction was carried out 3 times with 500 ml of ethyl acetate and the extracts were washed 3 times with 400 ml of water, dried, filtered and evaporated to dryness. The product was dissolved in 800 ml of methylene chloride, followed by filtration and evaporation to dryness. The product was crystallized from 20 ml of isopropyl ether and the crystals were separated out, washed with isopropyl ether and then dried at 80° C. under reduced pressure to obtain 5.1 g of the expected product melting at 159° C.

Analysis: $C_4H_4N_2O_2S$; molecular weight=144.15
Calculated: % C 33.33 % H 2.80 % N 19.43 % S 22.24
Found: 33.0 2.7 19.2 22.2

IR Spectrum (CHCl₃)

| | |
|---|---|
| —NH₂ | 3510 cm⁻¹ + 3380 cm⁻¹ |
| | 1608 cm⁻¹ |
| —NO₂ | 1554 cm⁻¹ |
| | 1328 cm⁻¹ |

STEP B: 3-tert-butyl carbonate-amino-2-nitro-thiophene 1.3 g of the product of Step A were dissolved at ambient temperature in 15 ml of anhydrous tetrahydrofuran and the solution was cooled down to +4° C. A solution of 2 g of ditertbutyl dicarbonate and 110 mg of 4-dimethylamino-pyridine in 15 ml of anhydrous tetrahydrofuran was introduced over 10 minutes. The resultant mixture was stirred for 30 minutes and then the solvents were evaporated off. The oil residue was purified by chromatography on silica (eluant: ethyl acetate-flugene 2-8) and the product was crystallized from 3 ml of isopropyl ether. The crystals were separated out, washed with isopropyl ether and dried under reduced pressure to obtain 2.13 g of expected product melting at 80° C.

Analysis: $C_9H_{12}N_2O_4S$; molecular weight=244.27
Calculated: % C 44.25 % H 4.95 % N 11.47 % S 13.13
Found: 44.4 4.9 11.5

STEP C: (3-tert-butyl-carbonate-amino-2-valerylamino-thiophene).

45 g of Raney nickel previously washed in water, 50 ml of valeric anhydride and 15 g of the product of Step B were mixed together at ambient temperature and hydrogenation was carried out at ambient temperature for 6 hours, followed by filtration, washing with methylene chloride and then evaportion to dryness. 150 ml of essence G were added and crystallization was started, followed by cooling down for one hour to about −10° C., separating and washing with essence G. The product was dried at about 80° C. under reduced pressure to obtain 12.5 g of product melting at 122° C. to 124° C. 30 mg of the expected product were obtained after 40 mg of the above product were crystallized from ethyl ether and it melted at 128° C.

IR Spectrum:

| | |
|---|---|
| =C—NH | 3426 cm$^{-1}$ |
| >=O | 1698 cm$^{-1}$ |
| | 1676 cm$^{-1}$ |
| Heterocycle | 1592 cm$^{-1}$ |
| + | 1520 cm$^{-1}$ |
| Amide II | 1500 cm$^{-1}$ |

STEP D; 2-tert-butyl-carbonate-amino-3-amino-thiophene trifluoroacetate 8.5 g of the product of Step C were introduced into 25 ml of trifluoroacetic acid over 10 minutes at about +5° C. and then the mixture was stirred at ambient temperature for 50 minutes. Evaporation to dryness was carried out and the oil was dissovled in 500 ml of ethyl ether at reflux, treated with activated charcoal and filtered. The filtrate was concentrated to 30 ml and 30 ml of isopropyl ether were added, followed by concentration to 40 ml, crystallizing, separating, washing with isopropyl ether, then with methylene chloride. The product was dried under reduced pressure at 70° C. to obtain 5.13 g of the expected product melting at 100° C. Crystallization from ethyl ether of 370 mg of the product yielded 240 mg of the expected product melting at 100° C.

Analysis: $C_{11}H_{15}F_3N_2O_3S$; molecular weight=312.313 Calculated: % C 42.30 % H 4.84 % F 18.25 % N 8.97 % S 10.27 Found: 4.8 18.6 8.9 10.3

IR Spectrum (Nujol) Absorption OH/NH complex region

| | |
|---|---|
| >=O | 1654 cm$^{-1}$ complex |
| Heteroaromatic | 1602 cm$^{-1}$ |
| Amide II | 1557 cm$^{-1}$ |
| | 1508 cm$^{-1}$ |
| CF$_3$: present | |

STEP E: 2-butyl-thieno-(2,3-d)-imidazole 940 mg of the product of Step D were dissolved at ambient temperature in 20 ml of water and 40 ml of a saturated solution of sodium carbonate were added. Extraction was carried out three times with 60 ml of methylene chloride and the combined extracts were dried, filtered and evaporated. The oil residue was dissolved at ambient temperature in 3 ml of phosphorous oxychloride and the mixture was stirred for 10 minutes at ambient temperature, then heated for one hour at reflux. The excess reagent was evaporated off and 30 ml of a saturated solution of sodium bicarbonate were added. Extraction was carried out 3 times with 60 ml of methylene chloride and the combined extracts were dried, treated with activated charcoal and evaporated to dryness. The product was dissolved in 300 ml of ethyl ether at reflux, filtered and concentrated to 5 ml. After crystallization, the product was separated out, washed with a few drops of ethyl ether and dried under reduced pressure at about 100° C. to obtain 400 mg of the expected product melting at 160° C.

Analysis: $C_9H_{12}N_2S$; molecular weight=180.27 Calculated: % C 59.96 % H 6.71 % N 15.54 % S 17.79 Found: 60.1 6.8 15.5 17.8

EXAMPLE 29

Methyl 4'-[(2-butyl-1H-thieno-(2,3-d)-imidazol-1-yl)-methyl]-(1,1'-biphenyl)-2-carboxylate (isomer A).

EXAMPLE 30

Methyl 4'-[(2-butyl-3H-thieno-(2,3-d)-imidazol-3-yl)-methyl]-(1,1'-biphenyl)-2-carboxylate (isomer B)

360 mg of the product of step E of Examples 29 and 30 were dissolved at ambient temperature in 7 ml of tetrahydrofuran and 96 mg of sodium hydride at 50% in oil were added in two lots at ambient temperature. After hydrogen had been released, the mixture was stirred for 10 minutes under nitrogen. Then, 610 mg of methyl bromomethyl-(1,1'-biphenyl-)-2-carboxylate (prepared according to EP 0,253,310) were added and the mixture was stirred at ambient temperature for 35 minutes. Then the solvent was evaporated off under nitrogen and 20 ml of water were added. Extraction was carried out with methylene chloride and the extracts were washed with water. The organic phase was dried, filtered and evaporated and the residue was chromatographed on silica (eluant: ethyl acetate 50-cyclohexane 50) to obtain 600 mg of isomer A (Rf=0.40) and 250 mg of isomer B (Rf=0.28).

NMR Spectrum (isomer A) CDCl$_3$ 250 MHz ppm

| | |
|---|---|
| CH$_3$ | 0.96 (t) |
| CH$_3$—$\underline{CH_2}$—(CH$_2$)$_2$— | 1.44 (m) |
| CH$_3$CH$_2$—$\underline{CH_2}$—CH$_2$ | 1.80 (m) |
| CH$_3$—(CH$_2$)$_2$—$\underline{CH_2}$ | 2.82 (t) |
| CO$_2$$\underline{CH_3}$ | 3.63 (s) |
| N—$\underline{CH_2}$—C$_6$H$_4$ | 5.29 (s) |
| S—$\underline{CH_2}$—CH$_2$ | 6.96 (d) |
| S—CH$_2$—$\underline{CH_2}$ | 6.64 (d) |

NMR Spectrum (isomer B) CDCl$_3$ 250 MHz ppm

| | |
|---|---|
| CH$_3$ | 0.96 (t) |
| CH$_3$—$\underline{CH_2}$—(CH$_2$)$_2$ | 1.47 (m) |
| CH$_2$—$\underline{CH_2}$—CH$_2$ | 1.84 (m) |
| CH$_3$—(CH$_2$)$_2$—$\underline{CH_2}$ | 2.87 (t) |
| CO$_2$$\underline{CH_3}$ | 3.63 (s) |
| N—$\underline{CH_2}$—C$_6$H$_4$ | 5.24 (s) |
| S—$\underline{CH_2}$—CH$_2$— | 7.11 (d) |
| S—CH$_2$—$\underline{CH_2}$— | 6.87 (d) |

EXAMPLE 31

4'[(2-butyl-1H-thieno-(2,3-d)-imidazol-1-yl)-methyl]-(1,1'-biphenyl)-2-carboxylic acid 600 mg of the product of Example 29 (isomer A) were dissolved at ambient temperature in 7 ml of methanol and 0.5 ml of 10N sodium hydroxide solution was added. After heating for one hour at reflux, the solvents were evaporated off and the dry extract was dissolved in 15 ml of water. The solution was cooled down and acetic acid was added until a pH of 4–5 was reached. After separation, the product was washed with water and dried under reduced pressure at 100° C. to obtain 400 mg of the expected product melting at 203° C.

Analysis: $C_{23}H_{22}N_2O_2S$; molecular weight=390.506 Calculated: % C 70.74 % H 5.68 % N 7.17 % S 8.21 Found:

70.8 5.6 7.1 8.2

IR Spectrum (Nujol)

| Acid with >=O | 1704 cm$^{-1}$ |
|---|---|
| Aromatic | 1595 cm$^{-1}$ |
| Heteroaromatic | 1504 cm$^{-1}$ |
| | 1516 cm$^{-1}$ |
| | 1482 cm$^{-1}$ |

EXAMPLE 32

4'-[(2-butyl-3H-thieno-(2,3-d)-imidazol-3-yl)-methyl]-(1,1'-biphenyl)-2-carboxylic acid Using the procedure of Example 31, 250 mg of the product of Example 30 (isomer B) in 4 ml of methanol and then the addition of 0.3 ml of sodium hydroxide (10N) were reacted to obtain 160 mg of the expected product melting at 203° C.

Analysis: $C_{23}H_{22}N_2O_2S$; molecular weight=390.506
Calculated: % C 70.74 % H 5.68 % N 7.17 % S 8.21 Found: 70.6 5.7 7.0 8.4

IR Spectrum (Nujol):

| >=O | 1710 cm$^{-1}$ |
|---|---|
| Aromatic | 1598 cm$^{-1}$ |
| Heteroaromatics | 1565 cm$^{-1}$ |
| | 1526 cm$^{-1}$ |
| | 1515 cm$^{-1}$ |

PREPARATION OF EXAMPLE 33

STEP A: 3-amino-4-valerylamino thiophene 3.06 g of 3,4-diaminothiophene were mixed with 45 ml of methylene chloride and 9 ml of triethylamine and a solution of 3.6 g of valeroyl chloride in 45 ml of methylene chloride was added at a temperature of 20° C. over one hour. The mixture was stirred for 30 minutes, followed by evaporation to dryness. After separation by chromatography (eluant: methanol/methylene chloride 5/95), 3.2 g of the expected monoamide were obtained which was crystallized from 15 ml of a 50/50 mixture of isopropyl ether and cyclohexane. The crystals were separated, washed with this mixture and dried under reduced pressure at 100° C. to obtain 2.14 g of the expected product melting at 110° C.

Analysis: $C_9H_{14}N_2OS$; molecular weight=198.288
Calculated: % C 54.52 % H 7.12 % N 14.13 % S 16.17
Found: 54.4 7.1 13.9 16.2

IR Spectrum ($CHCl_{31}$)

| NH | 3411 cm$^{-1}$ |
|---|---|
| | 3325 cm$^{-1}$ |
| >=O | 1678 cm$^{-1}$ |
| Conjugated system | 1615 cm$^{-1}$ |
| + | 1563 cm$^{-1}$ |
| Amide II | 1524 cm$^{-1}$ |
| + | 1502 cm$^{-1}$ |
| NH$_2$ deformation | |

STEP B: 2-butyl-thieno-[3,4-d]-imidazole 1 g of the product of Step A was dissolved at ambient temperature with stirring in 3 ml of phosphorous oxychloride and then the solution was heated at reflux for one hour. The solution was evaporated to dryness and 100 ml of a saturated aqueous solution of sodium bicarbonate were added. The mixture was stirred for 20 minutes at ambient temperature followed by extraction with methylene chloride. The extracts were washed with sodium bicarbonate solution and the organic phase was dried, filtered and evaporated. The oil was dissolved in 600 ml of ethyl ether at reflux, followed by filtration and evaporation to dryness to obtain 570 mg of product which was crystallized from 2 ml of isopropyl ether to obtain 500 mg of the expected product melting at 118° C.

NMR Spectrum CDCl$_3$ 60 MHz ppm

| S—CH$_2$ | 6.71 |
|---|---|
| —CH$_2$ | 2.68–2.80–2.91 |
| the central CH$_2$'s | 1.1 to 2.13 |
| CH$_3$ | 0.83–0.93–1.03 |

EXAMPLE 33

Methyl(4'-((2-butyl-1H-thieno-(3,4,-d)-imidazol-1-yl)-methyl)-(1,1'-biphenyl)-2-carboxylate 500 mg of the product of Step B of Example 33 were dissolved in 10 ml of anhydrous tetrahydrofuran and 120 mg of sodium hydride at 50% in oil were added. The mixture was stirred until the release of hydrogen was complete, then stirred under nitrogen for 10 minutes. 750 mg of methyl bromo methyl (1,1'-biphenyl)-2-carboxylate (prepared according to EP 0,253,310) were added and the mixture was stirred at ambient temperature for about 1 hour, followed by evaporation to dryness and extraction with methylene chloride. The extracts were washed with water, dried, filtered and evaporated to dryness. After chromatography on silica (eluant: ethyl acetate 5-cyclohexane 5), 1.14 of the expected product recovered.

The oil was crystallized from 2 ml of isopropyl ether and the crystals were separated out, washed with a few drops of isopropyl ether and dried under reduced pressure at 70° C. By two successive crystallization from isopropyl ether, 70 mg of the expected product melting at 120° C. were obtained.

Analysis: $C_9H_{12}N_2S$; molecular weight=180.27
Calculated: % C 59.96 % H 6.71 % N 15.54 % S 17.79
Found: 60.0 6.8 15.5 17.6

EXAMPLE 34

4'-((2-butyl-1H-thieno-(3,4-d)-imidazol-1-yl)-methyl)-(1,1'-biphenyl)-2-carboxylic acid 1.14 g of the product of Example 33 were dissolved at ambient temperature with stirring in 25 ml of methanol and 1 ml of sodium hydroxide was added. The mixture was refluxed for one hour. The methanol was evaporated off. The dry extract was dissolved in 75 ml of water and acetic acid was added until a pH of 6–5 was reacted. The mixture was stirred for 15 minutes followed by separation, washing with water and drying under reduced pressure at 80° C. to obtain 870 mg of the expected product melting at 168° C.

1.02 g of the product were dissolved in 50 ml of ethanol at reflux and 1 drop of acetic acid was added, then 40 ml of water were added. After crystallization, the crystals were separated, washed with a 50/50 mixture of water and alcohol and dried under reduced pressure at about 100° C. to obtain 900 mg of the desired product melting at 168° C. The product was dissolved in 100 ml of ethyl acetate at reflux and the solution was filtered. The filtrate was concentrated to about 50 ml and crystallized. The crystals were separated out, washed with ethyl acetate and dried under reduced pressure at about 100° C. to obtain 700 mg of the expected product melting at 168° C.

Analysis: $C_{23}H_{22}N_2O_2S$; molecular weight=390.506 Calculated: % C 70.74 % H 5.68 % N 7.17 % S 8.21 Found: 70.6 5.6 7.1 8.1

IR Spectrum (Nujol):

| | |
|---|---|
| $\rangle$=O | 1685 cm$^{-1}$ |
| Aromatic | 1597 cm$^{-1}$ |
| Heteroatom | 1520 cm$^{-1}$ |
| | 1487 cm$^{-1}$ |

PREPARATION OF EXAMPLE 35

STEP A: 5-bromo-2-butyl-1H-imidazole-4-methanol 10 g of 2-butyl-1H-imidazole-4-methanol (obtained by 0,253,310) were introduced into 150 ml of dioxane and 150 ml of 2-methoxyethanol with stirring and 12.7 g of N-bromo succinimide were added. The mixture was stirred at 40° C. for 2 hours and the reaction medium was allowed to cool down to ambient temperature for 90 minutes. After evaporation, the crystals were taken up in 250 ml of ethyl acetate and 150 ml of water and extraction was carried out with ethyl acetate. The extracts were washed with water, dried and filtered. Activated charcoal was added to the solution which was stirred for 10 minutes, followed by filtration and evaporation. The crystals were solubilized in 64 ml of hot ethyl acetate and then the solution stood for 90 minutes at 0° C. After separation, the crystals were washed with ethyl acetate, then with methylene chloride and separated and dried to obtain 4.39 g of the expected product melting at 160° C.

NMR Spectrum (DMSO ppm) 0.88 (t) CH$_3$—CH$_2$—CH$_2$—CH$_2$—C=1.29 (m) CH$_3$—CH$_2$—CH$_2$—CH$_2$—C=1.58 (m) CH$_3$—CH$_2$—CH$_2$—CH$_2$—C=2.55 (m) CH$_3$—CH$_2$—CH$_2$—CH$_2$—C=4.31 (sl) =C—CH$_2$—OH 5.10 (tl) =C—CH$_2$—OH 12.18 large absorption NH STEP B: 5-bromo-2-butyl-1H-imidazole-4-carboxaldehyde 4.37 g of the product of Step A were introduced into 130 ml of dioxane and then 16.32 g of manganese dioxide were added with stirring. The mixture was heated to approximately 100° C. for about 2 hours, then filtered. The filtrate was rinsed with dioxane and evaporated to obtain 3.72 g of the expected product melting at 113° C.

IR Spectrum CHCl$_3$, cm$^{-1}$

| | |
|---|---|
| =C—NH | 3418 cm$^{-1}$ |
| | 3222 cm$^{-1}$ |
| $\rangle$=O | 1655 cm$^{-1}$ |
| Heterocycle | 1545 cm$^{-1}$ |
| | 1504 cm$^{-1}$ |

STEP C: Methyl 4'-[[4-bromo-2-butyl-5-formyl-1H-imidazol-1-yl] -methyl]-(1,1'-biphenyl)-2-carboxylate 3.7 g of the product of Step B were introduced into 50 ml of dimethylformamide and 2.46 g of potassium bicarbonate were added with stirring. Then, the mixture stood for about 5 minutes and 5.86 g of methyl bromomethyl-(1,1'-biphenyl)-2-carboxylate (prepared according to EP 0,253, 310) in 55 ml of dimethylformamide were added. The mixture stood for 3 days at ambient temperature and the reaction medium was hydrolyzed with 100 ml of water, then extracted with ethyl acetate. The extracts were washed with water saturated with sodium chloride, dried, filtered and evaporated. After chromatography, (eluant: ethyl acetate 5-methylene chloride 95), 6.36 g of the expected product were recovered.

IR Spectrum (CHCl$_3$), cm$^{-1}$

| | |
|---|---|
| COOMe | 1726 cm$^{-1}$ |
| | 1434 cm$^{-1}$ |
| C=O (conjugated aldehyde) | approximately 1668 cm$^{-1}$ |
| Aromatic | 1600 cm$^{-1}$ |
| + | 1510 cm$^{-1}$ |
| Heterocycle | 1483 cm$^{-1}$ |

EXAMPLE 35

Ethyl 2-butyl-1-[(2'-(carboxy)]-(1,1'-biphenyl)-4-yl)-methyl] -1H-thieno-(2,3-d)-imidazole-5-carboxylate 149.5 mg of sodium ethylate were introduced into 5 ml of ethanol and 264 mg of ethyl acetate mercapto (prepared by 0,153,229 Patent of TEUTSCH ASZODI 85,211,781) in 2 ml of ethanol were added with stirring. 500 mg of the product of Step C in 12 ml of ethanol were added and the mixture was refluxed at about 78° C. with stirring for 24 hours. 149.5 mg of sodium ethylate and 264 mg of ethyl acetate mercapto were added and reflux was maintained for 3 hours. The solvents were eliminated and 400 ml of water were added. Extraction was carried out with methylene chloride and the extracts were dried, filtered and evaporated. After chromatography (eluant: ethyl acetate 5-methylene chloride 95), 322.5 mg of the expected product were recovered.

IR Spectrum (CHCl$_3$), cm$^{-1}$

| | |
|---|---|
| $\rangle$=O | 1716 cm$^{-1}$ |
| | 1698 cm$^{-1}$ |
| Conjugated system | 1600 cm$^{-1}$ |
| + | 1529 cm$^{-1}$ |
| Aromatic | 1512 cm$^{-1}$ |

EXAMPLE 36

2-butyl-1-((2'-carboxy-(1,1'-biphenyl)-4-yl)-methyl)-1H-thieno-(2,3-d)-imidazole-5 -carboxylic acid 295.4 mg of the product of Example 35 were introduced into 10 ml of ethanol and 1.55 ml of 2N sodium hydroxide were added drop-wise. The mixture stood at ambient temperature for 5 days with stirring and was then evaporated under reduced pressure. The residue was taken up in 8 ml of water. 1.55 ml of 2N hydrochloric acid were added, followed by filtering and drying under reduced pressure. The product was taken up in 9 ml of hot isopropanol and 4 ml of water were added, followed by filtering and drying to obtain 140 mg of the expected product melting at 264° C.

IR Spectrum (Nujol), cm$^{-1}$ Absorption OH/NH complex region

| | |
|---|---|
| >=O | 1708 cm$^{-1}$ |
| | 1650 cm$^{-1}$ |
| Aromatic | 1602 cm$^{-1}$ |
| + | 1519 cm$^{-1}$ ep |
| Heteroaromatic | 1504 cm$^{-1}$ |

PREPARATION OF EXAMPLE 37

STEP A: 1-1-dimethylethyl mercapto acetate

STEP ALPHA; 1,1-dimethylethyl thioacetate 35.24 g of potassium O-ethyldithiocarbonate were mixed with 150 ml of acetone at 0° to 2° C. and 39.16 g of 1-1-dimethylethyl bromoacetate were added over 10 minutes. The mixture was stirred at ambient temperature, then poured into 800 ml of ether, filtered and concentrated. The residue was taken up in 400 ml of ether, filtered and evaporated to obtain 49.58 g of the expected product.

STEP BETA: 1-1-dimethylethyl mercapto acetate

The product of Step Alpha was cooled down to 0° C. and 6.48 g of 1,2-diaminoethane were added dropwise. The mixture was stirred for 2 hours at ambient temperature and 200 ml of hexane were added, followed by stirring for about 10 minutes. Extraction of the residue was with hexane and the hexane solution was washed with 200 ml of 0.1N hydrochloric acid, then with 200 ml of sodium bicarbonate solution, dried and concentrated. The residue was distilled under reduced pressure to obtain 21.71 g of the expected product with a boiling point at 21 mm/Hg=72° C.

STEP B: Ethyl 3-amino-3-[(2-(1,1-dimethylethoxy)-2-oxoethyl)-thio]-2-[(1-oxopentyl)-amino]propenoate 5 g of ethyl 2-[(1-oxopentyl)-amino]-2-cyano ethanoate were mixed with 45 ml of methylene chloride and then 0.33 ml of triethylamine and 2.15 g of the product of Step A were added. The mixture was stirred at ambient temperature for 24 hours to obtain 8.49 g of expected product.

STEP C: Ethyl 2-butyl-5-[(2-(1,1-dimethylethoxy)-2-oxoethyl)-thio]-1H-imidazole-4-carboxylate 127 ml of methylene chloride and 9.81 g of phosphorous pentachloride were mixed together and the mixture was taken to − 78° C. 6.33 g of 4-dimethylamino-pyridine solubilized in 59 ml of methylene chloride were added dropwise and the mixture was stirred for 5 minutes. 8.49 g of the product of Step B were added and the mixture was stirred for a further 5 minutes at −78° C. The reaction medium was allowed to return to ambient temperature and was stirred for 24 hours. The reaction medium was poured into 400 ml of sodium bicarbonate and the mixture was stirred for 20 minutes, then left to settle and the aqueous phase was extracted with ethyl acetate. The organic phases were washed with water, dried, filtered and evaporated under reduced pressure to obtain 7.61 g of oil which was purified by chromatography on silica (eluant: ethyl acetate 10-methylene chloride 90) to obain 3.49 g of the expected product.

Analysis: $C_{16}H_{26}O_4N_2S$; molecular weight=342.45
Calculated: % C 56.117 % H 7.652 % N 8.18 % S 9.362
Found: 56.3 7.8 8 9.2

IR Spectrum (CHCl$_3$), cm$^{-1}$

| | |
|---|---|
| —NH | 3438 cm$^{-1}$ |
| | 3260 cm$^{-1}$ |
| Conjugated system | 1544 cm$^{-1}$ |
| | 1498 cm$^{-1}$ |
| >=O | 1726 cm$^{-1}$ |
| | 1672 cm$^{-1}$ complex |
| Me of tBu: | 1369 cm$^{-1}$ |

STEP D: Ethyl 2-butyl-1-[(2'-(methoxycarbonyl)-(1,1'-biphenyl)-4-yl)-methyl]-5-[(2-(1,1-dimethylethoxy)-2-oxoethyl)-thio]-1H-imidazole-5-carboxylate 1 g of the product of Step C was mixed with 6 ml of dimethylformamide and 450 mg of potassium bicarbonate were added. The mixture was stirred for 5 minutes at ambient temperature and then 1.07 g of methyl bromomethyl-(1,1'-biphenyl)-2-carboxylate (EP 0,253,310) solubilized in 6 ml of dimethylformamide were introduced. The mixture was stirred at ambient temperature for three days. The reaction medium was hydrolyzed with 500 ml of water and was extracted with ethyl acetate. The organic phase were washed with water, then with water saturated with sodium chloride, dried, filtered and evaporated to obtain 1.78 g of oil which was purified by chromatography on silica (eluant: ethyl acetate 2-methylene chloride 98) to obtain 1.381 g of the expected product.

IR Spectrum (CHCl$_3$) cm$^{-1}$

| | |
|---|---|
| Absence of NH | |
| C=O. | 1726 cm$^{-1}$ |
| | 1692 cm$^{-1}$ |
| Aromatic + | 1600 cm$^{-1}$ |
| Heterocycle | 1577 cm$^{-1}$ |
| | 1565 cm$^{-1}$ |
| | 1512 cm$^{-1}$ |
| | 1501 cm$^{-1}$ |

EXAMPLE 37

1,1-dimethylethyl-2-butyl-6-hydroxy-1-[(2'-(methoxycarbonyl)-(1,1'-biphenyl)-4-yl] -methyl]-1H-thieno-[4,5-b]-imidazole-5-carboxylate 47 mg of the product of Step D were mixed with 1 ml of tetrahydrofuran and the solution was cooled to −78° C. A lithium bistrimethylsilylamide solution at 1 mol/liter in 0.42 ml of tetrahydrofuran was added and the reaction medium was stirred at −78° C. for 2 hours, then allowed to return to ambient temperature over about 2 hours. The reaction medium was cooled down to −78° C. and then hydrolyzed with a 10% solution of acetic acid in tetrahydrofuran. The mixture was allowed to return to ambient temperature and evaporated under reduced pressure. The residue was taken up in 30 ml of ethyl acetate and the organic phase was washed with water and then with water saturated with sodium chloride. The organic phase was dried, filtered and evaporated to obtain 40 mg of a product which was purified by chromatography on silica (eluant: ethyl acetate 2-methylene chloride 98) to obtain 16.5 mg of the expected product.

NMR Spectrum 1H, ppm, (CDCl₃), 250 MHz

| | |
|---|---|
| 0.92(t) | CH₃ |
| 1.40(m) | \| |
| 1.76(m) | CH₂ |
| | \| |
| | CH₂ |
| 2.78(m) | \| |
| | CH₂—C= |
| 1.58(s) | CO₂tBu |
| 3.62(s) | CO₂CH₃ |
| 5.40(s) | N C̲H̲₂ C₆H₄ |
| 7.25(m) | —⟨phenyl⟩— |
| 7.41(dl) | H₃ |
| 7.41(dt) | H₄ H₅ |
| 7.53(dt) | |
| 7.84(dd) | H₆ |
| 10.55(m) | mobile 1H |

EXAMPLE 38

1,1-dimethylethyl 2-butyl-1-((2'-carboxy-(1,1'-biphenyl)-4-yl)-methyl)-6-hydroxy-1H-thien-(2,3-d)-imidazole-5-carboxylate 209 mg of the product of Example 37 were mixed with 12 ml of ethanol and 2 ml of 2N sodium hydroxide were added dropwise. The mixture stood at ambient temperature with stirring for 3 days and the reaction medium was evaporated to dryness. The residue was taken up in 10 ml of hot water and 2 ml of 2N hydrochloric acid were added, followed by filtering and drying under reduced pressure for 24 hours. 186 mg of product were obtained in powder form which was crystallized by solubilizing in 14 ml of hot isopropanol and 6 ml of water were added and cooled. The crystals were separated, washed with water and dried under reduced pressure at 40° C. for 24 hours to obtain 137.5 mg of the expected product melting at 221° C. to 222° C.

EXAMPLE 39

2-butyl-1-((2'-carboxy-(1,1'-biphenyl)-4-yl)-methyl)-6-hydroxy-1H-thien-(2,3 -d)-imidazole-5-carboxylic acid The above product was prepared starting with Example 38 by saponification of the CO₂tBu ester function to give COOH in position 5 of the thieno ring.

EXAMPLE 40

1,1-dimethylethyl 2-butyl-1-(2'carboxy-(1,1'-biphenyl)-4-yl)-methyl)-1H-thieno-(2,3 -d)-imidazole-6-carboxylate The above was prepared as in Example 37.

EXAMPLE 41

1,1-dimethylethyl-2-butyl-1-[(2'-(methoxycarbonyl)-(1,1'-biphenyl)-4-yl]-methyl]-1H-thieno-[4,5-b]-imidazole-6-carboxylate The above was prepared as in Example 38.

EXAMPLE 42

2-butyl-1-((2'-carboxy-(1,1'-biphenyl)-4yl)-methyl)-1H-thieno-(2,3-d)-imidazole-6-carboxylic acid The above was prepared as in Example 39.

EXAMPLE 43 OF PHARMACEUTICAL COMPOSITION

Tablets were prepared corresponding to the following formula:
Product of Example 10 . . . 10 mg
Excipient for a tablet completed at . . . 100 mg (detail of the excipient: lactose, talc, starch, magnesium stearate)

PHARMACOLOGICAL RESULTS

1—Test on the angiotensin II receptor

A fresh membrane preparation obtained from the liver of a rat was used and the tissue was ground up in a polytron in a Tris 50 mM buffer pH 7.4. The grinding was followed by 3 centrifugations at 30,000 g for 15 minutes and the deposits were taken up in between in the Tris buffer pH 7.4. The last deposits were suspended in an incubation buffer (Tris 20 mM, NaCl 135 mM, KCl 10 mM, glucose 5 mM, MgCl₂ 10 mM PMSF 0.3 mM, bacitracin 0.1 mM, BSA 0.2%) The aliquoted fractions of 2 ml were divided into hemolysis tubes and I¹²⁵ angiotensin II (25,000 DPM per tube) and the product to be studied were added. The product was first tested at $3 \times 10^{-5}$M three times. When the tested product displaced by more than 50% the radioactivity linked specifically to the receptor, it was tested again according to a range of 7 concentrations to determine the concentration which inhibited by 50% the radioactivity linked specificaly to the receptor. In this way, the 50% inhibiting concentration was determined.

The non-specific bond was determined by addition of the product of Example 94 of European Patent No. 0,253,310, at $10^{-5}$M (three times). The medium was incubated at 25° C. for 150 minutes, put in a water bath at 0° C. for 5 minutes, filtered under vacuum, rinsed with Tris buffer pH 7.4 and the radioactivity was counted in the presence of scintillating Triton. The results were expressed directly as the 50% inhibiting concentration (IC₅₀), that is as the concentration of studied product, expressed in nM, necessary to displace 50% of the specific radioactivity fixed on the receptor studied.

| Product | IC₅₀ in nanomoles |
|---|---|
| 34 | 789 |
| 5 | 1440 |
| 10 | 2270 |
| 2 | 2350 |
| 20 | 2715 |
| 15 | 3610 |
| 6 | 3460 |
| 27 | 89 |

2—Bringing to light the antagonistic activity of angiotensin II on the isolated portal vein The portal vein of male Wistar rats weighing about 350 g (IFFA Credo France) was removed after cervical dislocation and placed rapidly in a physiological solution (see below) at ambient temperature. A ring of about 1 mm was mounted in a bath having an isolated organ containing 20 ml of the following physiological solution (composition in mM: NaCl 118.3-KCl 14.7-MgSO₄ 1.2 -KH₂PO₄ 1.2-NaHCO₃ 25-glucose 11.1-CaCl₂ 2.5). The medium was maintained at 37° C. and oxygenated with an O₂ (95%), CO₂ (5%) mixture. The initial pressure imposed was 1 g, the rings were left at rest for 60 to 90 minutes. To avoid spontaneous contractions, verapamil was added to the incubation bath ($1.10^{-6}$M).

At the end of the rest period, angiotensin II (Ciba hypertensin) $3.10^{-8}$M was added to the incubation bath and left in contact with the preparation for 1 minute. This operation was repeated every 30 minutes with the tissue being washed 3 or 4 times between two stimulations by angiotensin. The compound to be studied was introduced into the bath 15 minutes before a new stimulation by angiotensin. From increasing concentrations of the molecule being applied, an $IC_{50}$ (concentration which produced a 50% inhibition of the response to angiotensin) can be calculated, this being expressed in nanomoles.

| Product | $IC_{50}$ in nanomoles |
|---|---|
| 10 | 3280 |
| 2 | 3400 |
| 5 | 3600 |
| 25 | 830 |

Various modificiations of the compounds and method of the invention may be made without departing from the spirit or scope thereof and it is to be understood that the invention is intended to be limited only as defined in the appended claims.

What is claimed is:

1. A compound selected from the group consisting of a compound of the formula

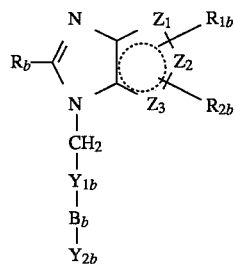

wherein $R_b$ is n-butyl or butenyl, one of $Z_1$, $Z_2$ and $Z_3$ is sulfur and the other two are =CH—, $R_{1b}$ and $R_{2b}$ are individually selected from the group consisting of hydrogen; halogen; —OH, —SH; alkoxy, alkyl and alkylthio of 1 to 6 carbon atoms, alkenyl and alkynyl of 2 to 6 carbon atoms, carbocyclic aryl, carbocyclic aralkyl and carbocyclic aralkenyl with up to 6 alkyl and alkenyl carbon atoms, all the alkyl, alkenyl, alkynyl, alkylthio, aryl, aralkyl and aralkenyl unsubstituted or substituted with at least one member of the group consisting of halogen, —OH, —SH, alkoxy and alkylthio of 1 to 4 carbon atoms, acyl and acyloxy; carboxy and carboxy esterified with alkyl of 1 to 4 carbon atoms, $Y_{1b}$ is phenyl, $B_b$ is a single bond or

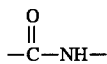

and when $B_b$ is a single bond or

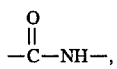

$Y_{2b}$ is phenyl unsubstituted or substituted with carboxy, esterified carboxy tetrazolyl, tetrazolyl-methyl or tetrazolyl-carbamoyl, —SO$_2$—$X_b$—$R_{14b}$, $X_b$ is selected from the group consisting of a single bond, —NH—, —CO— and

and $R_{14b}$ is selected from the group consisting of methyl, ethyl, vinyl, allyl, pyridylmethyl, pyridylethyl, pyridyl, phenyl and benzyl and when $B_b$ is a single bond, $Y_{2b}$ is cyano or free carboxy, salified or carboxy esterified with alkyl of 1 to 4 carbon atoms with the proviso that at least one of $R_{1b}$ and $R_{2b}$ is —OH and their non-toxic pharmaceutically acceptable salts with acid and base.

2. A compound of claim 1 selected from the group consisting of 1,1-dimethylethyl 2-butyl-1-[2'-carboxy-(1,1'-biphenyl)-4-yl)-methyl]-6-hydroxy-1H-thienyl-(2,3-d)-imidazol-5-carboxylate and its addition salts.

3. A compound of claim 1 selected from the group consisting of 2-butyl-[(2'-carboxy-(1,1'-biphenyl)-4-yl)-methyl]-6 -hydroxy-1H-thien-(2,3-d)-imidazole-5-carboxylic acid, 1,1-dimethylethyl 2-butyl-1-[(2'-(methoxycarbonyl)-(1,1'-biphenyl)-4-yl)-methyl]-1H-thieno-(4,5-b)-imidazole-6-carboxylate, 1,1-dimethylethyl 2-butyl-6-hydroxy-1-[(2'-(methoxycarbonyl)-(1,1'-biphenyl)-4-yl]-methyl-1H-thieno(4,5-b)-imidazole-5-carboxylate and 2-butyl-1-[)2'-carbonyl-1,1'-biphenyl)-4-yl)-methyl]-1H-thieno-(2,3-d)-imidazole-5-carboxylic acid.

4. Antagonistic angiotensin II receptor compositions comprising an antagonistically angiotensin II effective amount of at least one compound of claim 1 and an inert pharmaceutical carrier.

5. A composition of claim 4 selected from the group consisting of 1,1-dimethylethyl 2-butyl-1-[(2'-carboxyphenyl-)1,1'-biphenyl)-4-yl)-methyl]-6-hydroxy-1H-thienyl-(2,3-d)-imidazol-5 -carboxylate and its addition salts.

6. A method of inducing angiotensin II receptor antagonistic activity in warm-blooded animals comprising administering to warm-blooded animals an amount of at least one compound of claim 1 sufficient to induce angiotensin II receptor antagonistic activity.

7. A method of claim 6 wherein the compound is selected from the group consisting of 1,1-dimethyl 2-butyl-1-[(2'-carboxy-(1,1'-biphenyl)-4-yl)-methyl]-6-hydroxy-1H-thienyl-(2,3d)-imidazol-5-carboxylate and its addition salts.

8. A method of claim 6 wherein the compound is selected from the group consisting of 2-butyl-[(2'-carboxy-(1,1'-biphenyl)-4-yl)-methyl]-6-hydroxy-1H-thien-(2,3-d)-imidazole-5-carboxylic acid, 1,1-dimethylethyl 2-butyl-1-[(2'-(methoxycarbonyl)-(1,1' -biphenyl)-4-yl)-methyl]-1H-thieno-(4,5-b)-imidazole-6-carboxylate, 1,1-dimethylethyl 2-butyl-6-hydroxy-1-[(2'-(methoxycarbonyl)-(1,1'-biphenyl)-4-yl]-methyl-1H-thieno(4,5-b)-imidazole-5-carboxylate and 2-butyl-1-[(2'-carbonyl-1,1'-biphenyl)-4-yl)-methyl]-1H-thieno-(2,3-d)-imidazole-5-carboxylic acid.

* * * * *